(12) United States Patent
Mansfield

(10) Patent No.: US 8,859,094 B2
(45) Date of Patent: Oct. 14, 2014

(54) COMBINATION OF ELASTOMERIC FILM COMPOSITION AND ADHESIVE FOR A STRETCH LAMINATE

(71) Applicant: The Procter & Gamble Company, Cincinnati, OH (US)

(72) Inventor: Todd Leon Mansfield, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 49 days.

(21) Appl. No.: 13/673,304

(22) Filed: Nov. 9, 2012

(65) Prior Publication Data

US 2014/0134435 A1 May 15, 2014

(51) Int. Cl.

| | | |
|---|---|---|
| *B32B 7/12* | (2006.01) | |
| *B32B 27/00* | (2006.01) | |
| *C08J 5/18* | (2006.01) | |
| *B32B 27/08* | (2006.01) | |
| *A61L 15/24* | (2006.01) | |
| *C08L 53/02* | (2006.01) | |
| *B32B 27/30* | (2006.01) | |
| *A61F 13/49* | (2006.01) | |
| *C09J 153/02* | (2006.01) | |

(52) U.S. Cl.
CPC ............. *B32B 27/08* (2013.01); *C09J 153/025* (2013.01); *C08J 5/18* (2013.01); *C09J 153/02* (2013.01); *A61L 15/24* (2013.01); *C08L 53/025* (2013.01); *C08L 53/02* (2013.01); *B32B 27/30* (2013.01); *A61F 13/4902* (2013.01)
USPC ......................... 428/343; 428/355 R; 428/500

(58) Field of Classification Search
None
See application file for complete search history.

(56) References Cited

U.S. PATENT DOCUMENTS

| | | |
|---|---|---|
| 3,264,272 A | 8/1966 | Watkin |
| 3,645,992 A | 2/1972 | Elston |
| 3,806,003 A | 4/1974 | Fujimoto |
| 3,929,135 A | 12/1975 | Thompson |
| 4,151,240 A | 4/1979 | Lucas et al. |
| 4,243,314 A | 1/1981 | Bowe et al. |
| 4,324,246 A | 4/1982 | Mullane et al. |
| 4,463,045 A | 7/1984 | Ahr et al. |
| 4,552,709 A | 11/1985 | Koger et al. |
| 4,591,523 A | 5/1986 | Thompson |
| 4,798,081 A | 1/1989 | Hazlitt et al. |
| 4,808,178 A | 2/1989 | Aziz et al. |
| 4,909,803 A | 3/1990 | Aziz et al. |
| 5,151,092 A | 9/1992 | Buell et al. |
| 5,221,274 A | 6/1993 | Buell et al. |
| 5,554,145 A | 9/1996 | Roe et al. |
| 5,569,234 A | 10/1996 | Buell et al. |
| 5,580,411 A | 12/1996 | Nease et al. |
| 5,885,908 A | 3/1999 | Jaeger et al. |
| 6,004,306 A | 12/1999 | Roblet et al. |
| 6,120,487 A | 9/2000 | Ashton |
| 6,410,129 B2 | 6/2002 | Zhang et al. |
| 6,472,084 B1 | 10/2002 | Middlesworth et al. |
| 7,137,079 B2 | 11/2006 | Luo et al. |
| 7,307,031 B2 | 12/2007 | Carroll et al. |
| 7,626,073 B2 | 12/2009 | Catalan |
| 8,188,192 B2 | 5/2012 | Handlin et al. |
| 2002/0119301 A1* | 8/2002 | Zhang et al. ............... 428/318.6 |
| 2012/0207969 A1 | 8/2012 | Mansfield |
| 2012/0207996 A1 | 8/2012 | Chapman et al. |
| 2012/0208420 A1 | 8/2012 | Mansfield |
| 2012/0209230 A1 | 8/2012 | Mansfield |

FOREIGN PATENT DOCUMENTS

| | | |
|---|---|---|
| EP | 0 410 412 B1 | 1/1994 |
| EP | 0 422 108 B1 | 8/1994 |

OTHER PUBLICATIONS

All Office Actions, U.S. Appl. No. 13/026,533.
All Office Actions, U.S. Appl. No. 13/026,548.
All Office Actions, U.S. Appl. No. 13/026,563.
PCT International Search Report mailed Jan. 28, 2014 (9 pages).

* cited by examiner

*Primary Examiner* — Sheeba Ahmed
(74) *Attorney, Agent, or Firm* — William E. Gallagher

(57) ABSTRACT

A structure comprising an elastic film layer and an adhesive in contact therewith is disclosed. The elastomeric film layer may include a plasticizer and greater than 7 percent by weight of a tackifier. The elastomeric film formulation provides reduced loss of adhesion strength with the adhesive over time, providing for improvement in mechanical performance of the stretch laminate over time.

12 Claims, 12 Drawing Sheets

COMBINATION OF ELASTOMERIC FILM COMPOSITION AND ADHESIVE FOR A STRETCH LAMINATE

BACKGROUND OF THE INVENTION

Elastic materials, formed into elastic films, are commonly used for a wide variety of applications. For example, disposable absorbent articles typically include one or more components that rely on film materials, especially elastic film materials, to control the movement of liquids and to provide a comfortable, conforming fit when the article is worn by a wearer.

It is often useful to use adhesives to attach these elastic materials to other parts of the diaper. For example, laminating the elastic material to one or more nonwovens can provide benefits such as desirable look and feel, or facilitate the attachment of said laminate to other parts of the diaper. Sometimes, however, the mechanical integrity of adhesive bonds between elastomer and nonwoven can undergo an undesirable decrease as time elapses during distribution, storage and warehousing of product. Decreases in adhesion strength can be caused by undesired chemical interactions between adhesive and elastomer, and can lead to the mechanical failure of the elastic laminate or portions of the diaper to which it is attached.

Unintended mechanical failure of an article or article component is almost always undesirable, but when the article is a disposable absorbent article such as a diaper or training pant, the consequences of mechanical failure may be especially undesirable as a consequence of the possibility of bodily exudates escaping from the article, or the article separating from the wearer. Further compounding the potential problems associated with conventional films, it may in some circumstances be desired to use thinner or lower basis weight films, to reduce material costs. Problems associated with the formation of tears, holes, and apertures in a film may be even more acute in thinner/lower basis weight films.

Compositions for films addressed to the above-described problems are described in co-pending U.S. application Ser. No. 13/026,533.

With respect to improving the failure resistance of a laminate including an elastomeric film, selecting the composition of the film may be one approach that may be employed. Further, improvements in the other materials forming the laminate may be pursued. There is always room for any improvement that is both cost effective and effective at improving failure resistance of the composite laminate. Improvements that are synergistic in way that enables conservation of material quantities while providing parity or improvement in failure resistance are welcome by manufacturers and users of such laminates.

DETAILED DESCRIPTION OF THE INVENTION

Definitions

Figure 1:
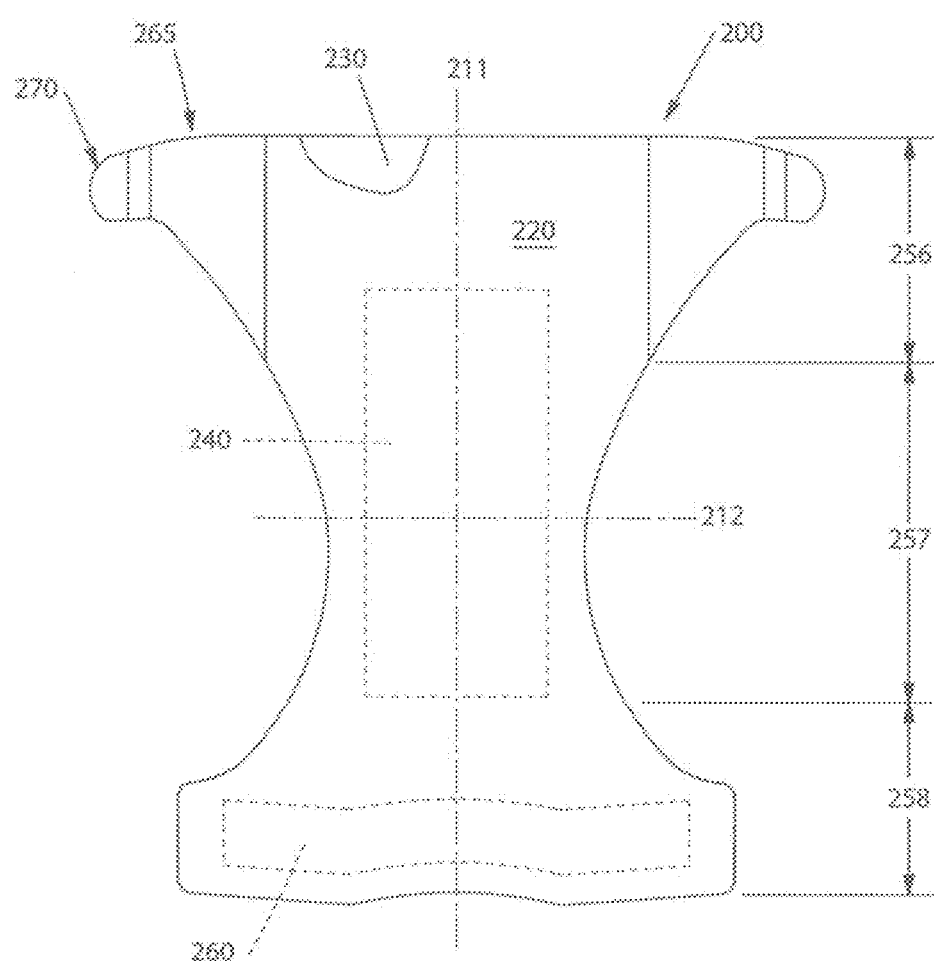
FIG. 1 is a plan view of an absorbent article.

"Absorbent article" means a device that absorbs and contains body exudates and, more specifically, devices that are placed against or in proximity to the body of the wearer to absorb and contain the various exudates discharged from the body. Exemplary absorbent articles include diapers, training pants, pull-on pant-type diapers (i.e., a diaper having a preformed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Activation" is the mechanical deformation of a plastically extensible material that results in permanent elongation of the extensible material in the direction of activation in the X-Y plane of the material. For example, activation occurs when a web or portion of a web is subjected to a stress that causes the material to strain beyond the onset of plasticity, which may or may not include complete mechanical failure of the material or portion of the material. Activation of a laminate that includes an elastic material joined to a plastically extensible material typically results in permanent deformation of the plastic material, while the elastic material returns substantially to its original dimension. "Activate," and variations thereof, means subjecting a material to an activation process.

"Aperture" means an opening in a film purposefully added during filmmaking or laminate making, which is intended to impart a desired characteristic such as breathability. The growth of an aperture is the increase in the size of the aperture due to mechanical failure of the portion(s) of the film adjacent to the aperture.

"Basis weight" is the mass of a sheet or web of material divided by its surface area. The units for basis weight herein are grams per square meter ($g/m^2$).

"Breathable" means a film or laminate that give Air Permeability Values of between 5 and 50 $m^3/m^2/min$ in the Air Permeability Test described below.

"Copolymer" means a polymer derived from two or more monomer species wherein the polymer chains each comprise repeat units from more than one monomer species.

"Crystalline melting temperatures" are determined by Differential Scanning calorimetry, which is described in more detail below. The melting endothermic peak temperature is taken as the $T_m$ ($T_{pm}$ per ASTM D3418-08) of a particular population of crystals. Materials of the current invention may have one or more melting endotherm peaks.

"Disposed" means an element is positioned in a particular place with regard to another element.

"Elastic," "elastomeric," and "elastically extensible" mean the ability of a material to stretch by at least 50% without rupture or breakage at a given load, and upon release of the load the elastic material or component exhibits at least 80% recovery (i.e., has less than 20% set) according to the Hysteresis Test described below. For example, a material with an initial gauge length of 25.4 mm is stretched to a length of 38.1 mm (50% engineering strain). During unstretching it retracts to a length of 29 mm when the tensile force decreases below 0.05 N. It thus has a set of 14.2% and is considered "elastomeric" by this definition. Stretch, sometimes referred to as strain, engineering strain, percent strain, draw ratio or elongation, along with recovery and set may each be determined according to the Hysteresis Test described in more detail below. It is to be understood, however, that this definition of elastic does not apply to materials that do not have the proper dimensions (e.g., not wide enough) to be properly subjected to the Hysteresis Test. Instead, such material is considered to be elastic if it can stretch to at least 50% upon application of a biasing force, and return substantially to its original length (i.e., exhibit less than 20% set) upon release of the biasing force at the same strain rate (and other conditions) as described in the Hysteresis Test below.

"Extensible" means the ability to stretch or elongate, without rupture or breakage, by at least 50%.

"Film" means a sheet-like, and skin- or membrane-like, material, not having by itself a macroscopically observable fibrous structure, wherein the length and width of the material far exceed the thickness of the material (e.g., 10×, 50×, or even 1000× or more). Films are typically formed from molten polymer resins through processes such as but not limited to extrusion, slot die coating, etc. Films are typically liquid impermeable but may be manufactured and/or further processed to render them air and/or vapor permeable.

"Hole" means an undesired opening in a film that can act as a "crack" in the Fracture Mechanics sense. The growth of a hole is the increase in the size of the hole due to mechanical failure of the portion(s) of the film adjacent to the hole.

"Hot Melt Adhesive" means an adhesive that contains from 20 percent to 65 percent by weight of a polymer component that when tested exhibits a tensile stress of between 0.5 MPa and 3.5 MPa at an elongation of 300 percent, according to ASTM D 412-06 A.

"Joined" means configurations whereby an element is directly secured to another element by affixing the element directly to the other element, and configurations whereby an element is indirectly secured to another element by affixing the element to intermediate member(s) that in turn are affixed to the other element.

"Laminate" means two or more materials that are bonded to one another by any suitable method known in the art (e.g., adhesive bonding, thermal bonding, ultrasonic bonding, or high pressure bonding using non-heated or heated patterned roll).

"Longitudinal" means a direction running substantially perpendicular from a waist end edge to an opposing waist end edge of an absorbent article when the article is in a flat out, uncontracted state. "Lateral" refers to a direction running from a side edge to an opposing side edge of an article and generally perpendicular to the longitudinal direction.

"Machine direction" or "MD" is the direction parallel to the direction of travel of the web in a manufacturing process. The "cross machine direction" or "CD" is the direction substantially perpendicular to the MD and in the plane generally defined by the web.

"Nonwoven" means a porous, fibrous material made from continuous (long) filaments (fibers) and/or discontinuous (short) filaments (fibers) by processes such as, for example, spunbonding, meltblowing, airlaying, coforming, carding, hydroentangling, and the like. Nonwovens do not have a woven or knitted filament pattern. Nonwovens may be liquid permeable or liquid impermeable as a result of fiber structure, size, density and surface properties (i.e. hydrophilic or hydrophobic).

"Plastic" and "plastically extensible" mean the ability of a material to stretch by at least 50% without rupture or breakage at a given load and, upon release of the load the material or component, exhibits at least 20% set (i.e., recovers less than 80%) according to the Hysteresis Test described below. For example, a material with an initial gauge length of 25.4 mm is stretched to a length of 38.1 mm (50% engineering strain). During unstretching it retracts to a length of 34.3 mm when the tensile force decreases below 0.05 N. It thus has a set of 35.0% and is considered "plastic" by this definition.

"Relaxed" means the state of an element, material or component at rest with substantially no external force acting on the element, other than gravity.

"Tear" means an undesired opening in a film that has intersected with one or more of the edges of the film, which can act as a "crack" in the Fracture Mechanics sense. The growth of a tear is the increase in the size of the tear due to mechanical failure of the portion(s) of the film adjacent to the tear.

"Web" means a material capable of being wound into a roll. Webs may be films, nonwovens, laminates, apertured films and/or laminates, and the like. The face of a web refers to one of its two dimensional surfaces, as opposed to its edge.

"X-Y plane" means the plane defined by the MD and CD of a moving web or the length and width of a piece of material.

Elastomeric Polymer Components

A number of elastomeric polymers can be used to make an elastic film. Nonlimiting examples of elastomeric polymers include homopolymers, block copolymers, random copolymers, alternating copolymers, graft copolymers, and the like. Particularly suitable polymers for use in films exhibiting resistance to tear propagation are block copolymers, which are typically made of blocks (or segments) of distinct repeat units that each contribute to the properties of the polymer. One reason block copolymers are recognized as being useful, at least in part, is because the blocks of the copolymer are covalently bonded to one another and form microphase-separated structures with rubber domains that provide good extensibility while the glassy end block domains provide mechanical integrity (e.g., good mechanical strength and avoidance of unwanted stress relaxation or flow). Block copolymers suitable for use herein may exhibit both elastomeric and thermoplastic characteristics. For example, the end-blocks may form domains that display stiff, rigid mechanical properties at temperatures that prevail during end use (e.g., 20° C.-40° C.), thereby adding rigidity and strength to the entire polymer. Such an end-block is sometimes referred to as a "hard block". The midblock may accommodate the relatively large deformations associated with elastomers and provides retractive force when the material is strained (i.e., stretched or extended). Such a midblock is sometimes referred to as a "soft block" or "rubbery block." Suitable block copolymers for use herein include at least one hard block (A) and at least one soft block (B). The block copolymers may have multiple blocks. In certain embodiments, the block copolymer may be an A-B-A triblock copolymer, an A-B-A-B tetrablock copolymer, or an A-B-A-B-A pentablock copolymer. Other suitable copolymers include triblock copolymers having endblocks A and A', wherein A and A' are derived from different compounds. In certain embodiments, the block copolymers may having more than one hard block and/or more than one soft block, wherein each hard block may be derived from the same or different monomers and each soft block may be derived from the same or different monomers.

Suitable hard block components have a glass transition temperature ($T_g$) greater than 25° C. or 45° C. or even 65° C., but typically less than 100° C. The hard block portion may be derived from vinyl monomers including vinyl arenes such as styrene and alpha-methyl-styrene or combinations thereof.

The soft block portion may be a polymer derived from conjugated aliphatic diene monomers. Typically, the soft block monomers contain fewer than 6 carbon atoms. Suitable diene monomers such as, for example, butadiene and isoprene may be used as-polymerized or in their hydrogenated form. Suitable soft block polymers include poly(butadiene), poly(isoprene), and copolymers of ethylene/propylene, ethylene/butene, and the like. In certain embodiments, it may be desirable to partially or fully hydrogenate any residual olefinic double bonds contained in the copolymer or portion thereof (e.g., midblock or endblock).

In a particularly suitable embodiment, the elastomeric polymer may be a styrene-ethylene-ethylene-propylene-styrene ("SEEPS") block copolymer that includes two polystyrene endblocks of approximately 8 kg/mol each and a 45 kg/mol midblock. The midblock may be formed, for example, by copolymerizing and then hydrogenating isoprene and butadiene. It may be desirable to hydrogenate the copolymer such that from 95-99% or even 98-99% of the original C=C double bonds in the midblock are saturated but the polystyrene endblocks remain aromatically intact. If the degree of hydrogenation is too low, the polymer may begin to lose its ability to undergo strain-induced crystallization. It is believed, without being limited by theory, that strain induced crystallization in a polymer is important for providing tear resistant characteristics to films made with such polymers. In certain embodiments, copolymerizing isoprene and butadiene to produce the rubbery midblock may result in a copolymer that varies both in comonomer sequence and in vinyl content. While a SEEPS copolymer is a block copolymer, the ethylene-ethylene-propylene ("EEP") midblock is more of a random copolymer than blocky or alternating. But subtle departures from randomness may occur. The departures from randomness, as well as the vinyl content of the copolymer, may be controlled by adjusting the conditions during polymerization. For example, copolymerization of isoprene and butadiene with subsequent hydrogenation may give rise to a variety of branch types. Table 1 below exemplifies the different branch types that may result. With the partial exception of the methyl branches, the branches typically do not "fit" into the polyethylene-type crystals, and therefore decrease the midblock's degree of crystallinity and $T_m$. For example, the midblock of a SEEPS block copolymer may be approximately 7% crystalline at temperatures below −50° C. and have a $T_m$ of approximately 0° C. In comparison, a substantially unbranched polyethylene is approximately 75% crystalline and has a $T_m$, of approximately 135° C.

TABLE 1

| Isomer | Branch Type After Hydrogenation |
|---|---|
| 1,2 Isoprene | Methyl, Ethyl |
| 3,4 Isoprene | Isopropyl |
| 1,4 Isoprene | Methyl |
| 1,2 Butadiene | Ethyl |
| 1,4 Butadiene | No branch - possible to crystallize |

The length of the runs of crysallizable $CH_2$ sequences, which directly impact the melting temperature of the polymer midblock, depends, at least partially, on the sequence of comonomer incorporation into the midblock (e.g., isoprene always gives a branch of some type) and the overall balance between 1,4 and 1,2 (or 3,4) polymerization of the dienes. The $T_m$ of the crystal may provide information about the length of the crystallizable sequences and the ability of the material to undergo strain-induced crystallization, both of which are related to the number, type, and distribution of the branches on the midblock backbone. Suitable elastomers herein include sufficiently long crystallizable sequences of $CH_2$ groups (which form polyethylene-type crystals) that have a $T_m$ of greater than 10° C. (compared to, e.g., −5° C. for previously known materials). A suitable $T_n$, for the elastomers herein is between 10° C. and 20° C., 12° C. and 18° C.; 13° C. and 17° C.; or even between 14° C. and 16° C.

In addition to the EEP midblocks described above, it may be desirable to provide a midblock of the "EB" type (i.e., hydrogenated polybutadiene) that contains similar crystallizable sequences, for example, by choosing the appropriate solvent polarity (which controls 1-4 vs. 1-2 content), as described in *Anionic Polymerization: Principles and Practical Applications*, Henry Hsieh, Roderick Quirk; Chapter 9, pp. 197-229; Marcel Decker, New York (1996).

Film Characteristics

Unlike conventional elastomeric films (e.g., films formed from known elastomers such as Vector 4211 from Dexco Polymers L. P., Houston, Tex.), which form films that exhibit minimal or no tear resistance, the elastic films disclosed herein include an effective amount of at least one elastic polymer that imparts suitable tear resistance to the film. It is to be appreciated that such resistance is not limited to tears, but also includes slits, apertures, openings, holes, and/or any other discontinuities in the film. The Slow Tear Test, described in more detail below, provides a suitable method for quantifying a film's resistance to the growth of a tear, hole, aperture, or other discontinuity. Suitable time-to-fail values for films disclosed herein include values of greater than 1 hour, 2 hours, 4 hours, 6 hours, 10 hours, 15 hours, or even up to 24 hours or more, for example up to 30 hours, 36 hours, 40 hours, 44 hours, 48 hours, or even up to 60 hours when measured according to the Slow Tear Test. Ideally, the film is capable of resisting the growth of a tear indefinitely. While the present films desirably provide suitable resistance to the growth of a tear as described herein, it may also be desirable for the films herein to exhibit resistance to the rapid application of a relatively high amount of mechanical stress. For example, the present films may have a High-Speed Tensile Strength of between 10 and 25 MPa; 15 and 20 MPa; 16 and 19 MPa; or even between 17 and 18 MPa when measure according to the High Speed Tensile Test described in more detail below. It may also be desirable to provide a film that exhibits a Notched High Speed Tensile Strength of between 10 and about 20; MPa; 14 and 19 MPa; or even between 15 and 18 MPa when measure according to the Notched High-Speed Tensile Strength Test described in more detail below. It is believed, without being limited by theory, that suitable High Speed Tensile and/or Notched Tensile Strengths in a film may be important for providing at least some resistance to film failure related to relatively high rates of undesired mechanical stress.

The present tear resistant films are not limited to any particular dimension, and may be configured as relatively thin sheets of material. In certain embodiments, the film may have an Effective Average Thickness, of between 1 μm-1 mm; 3 μm-500 μm; or 5 μm-100 μm, or any value in these ranges. Suitable basis weight ranges for the films disclosed herein include from 20 to 140 $g/m^2$, for example from 25 to 100 $g/m^2$; from 30 to 70 $g/m^2$; or even from 35 to 45 $g/m^2$. The tear resistant films may be formed by any suitable method in the art such as, for example, extruding a molten thermoplastic and/or elastomeric polymer through a slit die and subsequently cooling the extruded sheet. Other non-limiting examples for making films include casting, blowing, solution casting, calendering, and formation from aqueous or cast, non-aqueous dispersions. Suitable methods of producing films from polymeric materials are described in *Plastics Engineering Handbook of the Society of the Plastics Industry, Inc.*, Fourth Edition, 1976, pages 156, 174, 180 and 183. In certain embodiments, the elastic film may have a loading engineering stress at 200% strain (L200) of between about 0.8 and 2 MPa, 1.0 and 1.5 MPa, or even between 1.0 and 1.2 MPa, and an unloading engineering stress at 50% strain (UL50) of between 0.3 and 0.8, 0.4 and 0.6, or even between 0.5 and 0.6 MPa according to the Hysteresis Test described in more detail below. The L200 and UL50 values disclosed above may be important for providing a film that is suitable for use in a disposable absorbent article (e.g., for providing low force recovery stretch, a snug comfortable fit, less undesired sag, containment of bodily exudates in a desired location, strength to resist the initial formation of a hole or tear).

Additives

The present tear resistant films may include one or more additives commonly used in the art to tailor a film for a particular use. For example, stabilizers, antioxidants, and bacteriostats may be employed to prevent thermal, oxidative, and bio-chemical degradation of the film or film component. In certain embodiments, it may be desirable to include a modifying resin in the film composition to provide desirable elastic recovery characteristics, for example, as disclosed in U.S. Pat. No. 7,717,893 to Hird, et al. Generally, the additive or additives may account for 0.01% to 60%; 0.01% to 25%; or even 0.01% to 10% of the total weight of the film.

Suitable examples of stabilizers and antioxidants are well known in the art and include high molecular weight hindered phenols (i.e., phenolic compounds with sterically bulky radicals in proximity to the hydroxyl group), multifunctional phenols (i.e., phenolic compounds with sulfur and phosphorous containing groups), phosphates such as tris-(p-nonylphenyl)-phosphite, hindered amines, and combinations thereof. Representative hindered phenols include t-butylhydroxyquinone; 1,3,5-trimethyl-2,4,6-tris(3-5-di-tert-butyl-4-hydroxybenzyl)benzene; pentaerythritoltetrakis-3(3,5-di-tert-butyl-4-hydroxyphenyl)propionate; n-octadecyl-3(3,5-ditert-butyl-4-hydroxyphenyl)propionate; 4,4'-methylenebis (4-methyl-6-tert butylphenol); 4,4'-thiobis(6-tert-butyl-o-cresol); 2,6-di-tert-butylphenol; 6-(4-hydroxyphenoxy)-2,4-bis(n-ocytlthio)-1,3,5-triazine; 2,4,6-tris(4-hydroxy-3,5-di-tert-butyl-phenoxy)-1,3,5-triazine; di-n-octadecyl-3,5-di-tert-butyl-4-ydroxybenzylphosphonate; 2-(n-octylthio) ethyl-3,5-di-tert-butyl-4-hydroxybenzoate; and sorbitol hexa-(3,3,5-di-tert-butyl-4-hydroxy-phenyl)propionate. Proprietary commercial stabilizers and/or antioxidants are available under a number of trade names including a variety of WINGSTAY, TINUVIN and IRGANOX products.

Examples of suitable bacteriostats include benzoates, phenols, aldehydes, halogen containing compounds, nitrogen compounds, and metal-containing compounds such as mercurials, zinc compounds and tin compounds. A representative bacteriostat is 2,4,4'-trichloro-2'-hydroxy-diphenyl-ether which is available under the trade designation IRGASAN PA from Ciba Specialty Chemical Corporation, Tarrytown, N.Y.

Other optional additives include thermoplastic polymers or thermoplastic polymer compositions which preferentially associate with the hard blocks or segments of the block copolymers. Without intending to be bound by theory, it is believed that these thermoplastic polymers become incorporated into the entangled three-dimensional network structure of the hard phase. This entangled network structure can provide improved tensile, elastic and stress relaxation properties of the elastomeric composition. Where the elastomeric polymer comprises a styrenic block copolymer, thermoplastic polymer additives such as polyphenylene oxide and vinylarene polymers derived from monomers including styrene, alpha-methyl styrene, para-methyl styrene, other alkyl styrene derivatives, vinyl toluene, and mixtures thereof, are useful herein because they are generally considered to be chemically compatible with the styrenic hard blocks of the block copolymer.

Various viscosity modifiers, plasticizers, slip agents or anti-block agents can be employed as additives to provide improved handling characteristics or surface characteristics. Plasticizers include processing oils, which are well known in the art and include synthetic and natural oils, naphthenic oils, paraffinic oils, olefin oligomers and low molecular weight polymers, vegetable oils, animal oils, and derivatives of such including hydrogenated versions. Plasticizing oils also may incorporate combinations of such oils. A particularly suitable plasticizing oil is mineral oil. Viscosity modifiers are also well known in the art. For example, petroleum derived waxes can be used to reduce the viscosity of the elastomeric polymer in thermal processing. Suitable waxes include low number-average molecular weight (e.g., 600-6000) polyethylene; petroleum waxes such as paraffin wax and microcrystalline wax; atactic polypropylene; synthetic waxes made by polymerizing carbon monoxide and hydrogen such as Fischer-Tropsch wax; and polyolefin waxes.

Various colorants and fillers are known in the art and may be included as additives in the film composition. Colorants can include dyes and pigments such as titanium dioxide. Fillers may include such materials as talc and clay. Other additives may include dyes, UV absorbers, odor control agents, perfumes, fillers, dessicants, and the like.

Apertures or Pores; Breathability Features

In certain embodiments, it may be desirable to provide pre-formed apertures (i.e., apertures that are intentionally provided in the film during a manufacturing process) that extend through the thickness of the film. The apertures may have any suitable size and/or shape desired. For example, the apertured film may have circle-shaped, individual apertures with a diameter of between 0.2 and 3 mm and an open area of 5-60% (e.g., 10-30% or 15-25%). In another example, the apertured film may include slits that can "opened up" by applying a transverse force to form round, rectangular, diamond-shaped apertures, combinations of these, and/or any other suitable shape desired with a largest dimension in the x-y plane of the film of between 0.2 and 3 mm. In still another example, the apertures may extend three-dimensionally through the film and form a cone-like structure. In such an example, the tapered, cone-like structure may include a first opening having a first diameter in the plane of the film (major diameter) and a second opening having a second, smaller diameter at the opposing end of the cone (minor diameter). Aperture size and open area are measured according to the method set forth in U.S. Publication No. 2007/0073256 filed by Ponomorenko, et al., on Sep. 22, 2006 and titled "Absorbent Article With Sublayer." Suitable methods for forming apertures in a film are commonly known in the art and include, for example, die punching, slitting, hot-pin melt aperturing, vacuum forming, high pressure jet aperturing, embossing rolls, combinations of these and the like. In conventional films, aperture pattern selection may be largely dictated by the need to minimize stress concentration around the apertures, thereby mitigating the risk of tearing the film during mechanical activation. But the film disclosed herein is not so limited, and therefore may provide improved manufacturing flexibility when selecting an aperture pattern and/or size. Suitable examples of apertured films and methods of aperturing films are disclosed in U.S. Pat. No. 6,410,129 issued to Zhang, et al., on Jun. 25, 2002 and titled "Low Stress Relaxation Elastomeric Materials;" U.S. Pat. No. 7,307,031 issued to Carroll, et al., on Dec. 11, 2007 and titled "Breathable composite sheet structure and absorbent articles utilizing same;" U.S. Pat. No. 4,151,240, issued to Lucas et al., on Apr. 24, 1979 and titled "Method for Debossing And Perforating A Running Ribbon Of Thermoplastic Film;" U.S. Pat. No. 4,552,709 issued to Koger, I I, et al., on Nov. 12, 1985 and titled "Process For High-Speed Production Of Webs Of Debussed And Perforated Thermoplastic Film;" U.S. Pat. No. 3,929,135, to Thompson, issued on Dec. 30, 1975 and titled "Absorptive Structures Having Tapered Capillaries;" U.S. Pat. No. 4,324,246 issued to Mulvane, et al. on Apr. 13, 1982 and titled "Disposable Absorbent Article Having A Stain Resistant Topsheet;" U.S. Pat. No. 4,342,314, issued to Ravel, et al., on Aug. 3, 1982 and titled "Resilient Plastic Web Exhibiting Fiber-Like Properties;" U.S. Pat. No. 4,463,045 issued to Air, et al., on Jul. 31, 1984 and titled "Macroscopically Expanded Three-Dimensional Plastic Web Exhibiting Non-Glossy Visible Surface and Cloth-Like Tactile Impression;" and U.S. Pat. No. 4,591,523 issued to Thompson on May 27, 1986 and titled "Apertured Macroscopically Expanded Three-Dimensional Polymeric Web Exhibiting Breathability And Resistance To Fluid Transmission."

EXAMPLES

Table 2 shows the weight percent of components in formulas for making various film Samples. The S4033, JL-007, and JL-014 shown in Table 2 are hydrogenated SEEPS block copolymers available from Kuraray America, Inc. in Pasadena, Tex. S4033 is a known SEEPS block copolymer, while the JL series (e.g., JL-007 and JL-014) may be thought of as S4033-type block copolymers modified for improved processability. The JL-series of SEEPS block copolymers have a mass ratio of isoprene to 1,3 butadiene of from 46/54 to 44/56 (e.g., 45/55). The Oil in Table 2 is a white mineral oil such as DRAKEOL 600, HYDROBRITE 550, or KRYSTOL 550. REGALREZ 1126 and REGALITE 1125 are tackifiers available from Eastman Chemical Company in Kingsport, Tenn. The PS 3190 is a polystyrene homopolymer available from NOVA Chemical Company, Canada. The material designated as "AO" is a suitable antioxidant such as IRGANOX 100 available from Ciba Specialty Chemicals in Switzerland.

Samples 1-11 are produced by extruding a thermoplastic composition through a slot die to form a film that is 100 mm wide and 100 μm thick. The thermoplastic composition is formed by extruding material in a Leistritz (27 mm) twin screw extruder with extended mixing sections. First, the oil and SEEPS polymers are mixed together, and then the polystyrene and tackifier are blended into the mixture, which is then fed into the extruder. Temperatures in the extruder typically range from 170-230° C. Subsequently, the compositions are formed into films using a ThermoFisher 20 mm single screw extruder. Temperatures in the ThermoFisher extruder typically range from 170-230° C.

TABLE 2

| Ingredient | Sample No. | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| 4033 | | | | | | | 60 | | | | 56 | 56 | | | |
| JL-007 | 55 | 60 | 60 | 60 | | 55 | | | 60 | 56 | | | 56 | | |
| JL-013 | | | | | | | | | | | | | | | 56 |
| JL-014 | | | | | 55 | | | 60 | | | | | | 56 | |
| Oil | 15 | 20 | 20 | 16 | 15 | 15 | 20 | 20 | 20 | 31 | 31 | 31 | 31 | 31 | 31 |
| Regalrez 1126 | 15 | 10 | 15 | 16 | 15 | | 10 | 10 | | | | | | | |
| Regalite 1125 | | | | | | 15 | | | 10 | | | | | | |
| PS 3190 | 15 | 10 | 5 | 8 | 15 | 15 | 10 | 10 | 10 | 13 | 13 | 13 | 13 | 13 | 13 |
| AO | 0.05 | | | | 0.05 | 0.05 | | | | 0.1 | 0.1 | | | | |

Table 3 illustrates the time-to-fail and melt temperatures of various elastomeric film materials. Samples 1-6 and 9-10 are provided to show suitable examples of the present film. Samples 7 and 11 are provided as comparative examples to show that not all SEEPS block copolymers necessarily provide suitable tear resistance and/or processability. The time-to-fail measurements are obtained according to the Slow Tear Test and the $T_n$, values are obtained according to the DSC method. Samples 12-15 in Table 3 are formed by a two-stage compression molding procedure where the elastomer is compressed between heated platens (215° C.) and held for a dwell time of 3 minutes using shims that give a thick sheet of elastomer (approximately 2.5 mm thick) then subsequently folding and stacking the thick film and pressing without a shim and holding for a dwell time of about 30 seconds to give a film of between 80-200 μm in thickness. The percentages of the various ingredients are all weight percentages based on the weight of the film. Sample 12 is provided as a comparative example and is formed from 56% S4033, 13% PS3160, and 31% white mineral oil. Samples 13-15 include the same relative amounts of SEEPS block copolymer, polystyrene homopolymer, and mineral oil as Sample 12, but vary in the kind of SEEPS copolymer, including the $T_n$, of the polymer, used in their formation. Sample 13 is formed using 56% JL-007. Sample 14 is formed using JL-014. Sample 15 is formed using JL-013. These ingredients are added to a small batch mixer (Haake) and mixed at 50 RPM at a temperature of 210° C. for 3 minutes. Sheets are subsequently produced by pressing between heated platens held at 210° C.

TABLE 3

| Sample No. | time-to-fail (hr.) | $T_m$ (° C.) |
|---|---|---|
| 1 | 7.2 | 17.7 |
| 2 | 8.3 | 16.1 |
| 3 | 31.5 | 15.1 |
| 4 | 17.5 | 16.2 |
| 5 | 13.7 | 14.5 |
| 6 | 11.6 | 16.6 |

TABLE 3-continued

| Sample No. | time-to-fail (hr.) | $T_m$ (° C.) |
|---|---|---|
| 7 | 1.6 | 2.4 |
| 8 | 9.6 | 13.9 |
| 9 | 10.2 | 15.7 |
| 10 | 0.9 | 14.6 |
| 11 | 0.3 | 1.8 |
| 12 | 0.5 | −1.0 |
| 13 | 2.1 | 13.0 |
| 14 | 0.8 | 13.0 |
| 15 | 7.0 | 18.0 |

As can be seen Table 3, the Samples that include the S4033 SEEPS block copolymer fail to provide a time-to-fail of about an hour or more and/or a $T_m$, of between 10 to 20° C., whereas the samples formed from the JL-series of SEEPS block copolymers provide these desired properties.

Table 4 below illustrates the High Speed Tensile Strength and Notched High Speed Tensile Strength of film samples 13, 14, 15, and 11 from Table 3. As can be seen in Table 4, Samples 13-15 are still able to provide suitable High Speed Tensile Strength and Notched High Speed Tensile Strength in addition to slow tear resistance.

TABLE 4

| No. | Sample ID | High Speed Tensile Strength (MPa) | Notched High Speed Tensile Strength (MPa) |
|---|---|---|---|
| 11 | grf410-16-comp | 20.6 | 13.9 |
| 13 | SC1163 | 21.1 | 18.2 |
| 14 | SC1164 | 20.8 | 15.4 |
| 15 | SC1165 | 19.7 | 16.5 |

Laminate; Adhesives; Modifications to Compositions

In certain embodiments, it may be desirable to incorporate the film into a laminate such as, for example, a tri-laminate structure with one or more film layers sandwiched between two or more nonwoven layers (e.g., a film layer sandwiched between two SMS nonwoven layers). Suitable examples of laminate structures are disclosed in co-pending U.S. Ser. No. 13/026,548, filed on Feb. 14, 2011 by Mansfield, titled "Tear Resistant Laminate" and further identified as P&G attorney Docket No. 11994 and U.S. Publication No. 2007/0249254 filed by Mansfield on Apr. 24, 2006 and titled "Stretch Laminate, Method of Making and Absorbent Article."

Adhesives

A nonwoven web material may be adhered to a film by an adhesive, such as a hot melt adhesive. Described below are examples of potential suitable adhesives.

Block Copolymer-Based Hot Melt Adhesives

In one group of embodiments, an adhesive composition may contain a block copolymer component that contains one or more block copolymers in an amount ranging from about 10 wt-% to about 45 wt-%, preferably from about 15 wt-% to about 30 wt-% and most preferably from about 20 wt-% to about 30 wt-%.

A wide variety of block copolymers may be useful including A-B-A triblock structures, A-B diblock structures, (A-B)n radial block copolymer structures, as well as branched and grafted versions of such, wherein the A endblock is a non-elastomeric polymer block, typically including polystyrene, and the B block is an unsaturated conjugated diene or hydrogenated version thereof. In general, the B block is typically isoprene, butadiene, ethylene/butylene (hydrogenated butadiene), ethylene/propylene (hydrogenated isoprene), and mixtures thereof. The block copolymers including an unsaturated conjugated diene such as styrene-isoprene-styrene (SIS), styrene-butadiene-styrene (SBS) and mixtures thereof may be preferred due to their increased tack and reduced cost. Commercial embodiments include the KRATON D series block copolymers, available from Shell Chemical Company (Houston, Tex.), EUROPRENE SOL T block copolymers available from EniChem (Houston, Tex.), VECTOR block copolymers available from Exxon (Dexco) (Houston, Tex.), and SOLPRENE block copolymers from Housmex (Houston, Tex.) as well as others.

In addition to the block configuration, block copolymers are typically characterized according to their reported styrene content, diblock content, and in terms of their melt flow rate (MFR, Condition G) or solution viscosity, which relates to the molecular weight of the block copolymer.

Typically, the non-elastomeric A block (styrene) concentration ranges from about 5 wt-% to about 45 wt-% with respect to the total weight of the block copolymer. The styrene portion is less susceptible to heat degradation. Accordingly, hot melt adhesive compositions based on higher styrene content block copolymers generally exhibit enhanced heat stability relative to hot melt adhesive compositions based on block copolymer having a lower styrene content. However, high styrene content (>30%) are typically not available in low melt flow rate grades. Since employing at least one block copolymer having a low melt flow rate may be useful, in may be preferred that the styrene content of the copolymers ranges from about 15 wt-% to about 30 wt-% with respect to the total weight of the block copolymer.

In general, block copolymers range in AB diblock content from 0, wherein the block copolymer is 100% coupled, as in the case of several grades of the VECTOR block copolymers, to 100% diblock, as in the case of multi-arm (EP)n8 block copolymers. For increased tack and improved adhesion, it may be preferred that one or more of the block copolymers be employed in the adhesive contain diblock. More particularly, the diblock content of such block copolymers may range from about 20 wt-% to about 50 wt-%.

The molecular weight of a block copolymer is related to its melt flow rate (MFR) and its solution viscosity at 77° F. for a given weight of polymer in toluene. Generally, a MFR is reported for grades of block copolymers that are sufficiently low enough in molecular weight such that the MFR can be measured according to Condition G (ASTM-1238, 200° C./5 kg). For block copolymers in which the molecular weight is too high to measure the MFR, a solution viscosity is typically reported by the supplier. The amount of block copolymer employed for determining the solution viscosity varies depending on the molecular weight. For the high molecular weight block copolymers, the solution viscosity may be expressed as a function of a 10 wt-% or 15 wt-% block copolymer solution, whereas for more conventional and moderate molecular weight block copolymers, a 25 wt-% block copolymer solution is employed. It may be preferred that the adhesive include at least one block copolymer having a melt flow rate of less than about 20 g/10 min. or even about 15 g/10 min or less.

The adhesive composition may include a blend of block copolymer wherein the first block copolymer is relatively soft, or low in modulus, in comparison to the second block copolymer. According the first (soft) block copolymer typically differs from the second block copolymer with regard to the selection of midblock, the structure of the block copolymer, the styrene content, and the diblock content.

The first block copolymer is typically an SIS block copolymer having a styrene content of about 30 wt-% or less, or about 20 wt-%, or even about 15% styrene or less, relative to the total weight of the block copolymer. The first block copolymer may be 100% triblock and thus not contain any appreciable diblock. It may be preferred however, that the first block copolymer contains a diblock in amount greater than 20 wt-% of the total weight of the block copolymer and more preferably about 30 wt-% diblock or greater. In a particular embodiment, the soft block copolymer component is a blend of a linear SIS block copolymer and a radial SIS block copolymer, each having a diblock content of at least 20 wt-%.

The second block copolymer may also be SIS, or SBS or even radial SBS. The second (hard) block copolymer typically has a styrene content of about 30 wt-% or greater. In the case of block copolymer having a styrene content of greater than 40 wt-% the melt flow rate is typically relatively high, about 30 MFR or greater. It may be preferred that the second block copolymer has a styrene content of about 30 wt-% or lower and a melt flow rate of less than 10 g/10 min. It may be further preferred that the second block copolymer be sufficiently high in molecular weight such that the solution viscosity, rather than the melt flow rate is reported. In a particular embodiment the solution viscosity of the second block copolymer is greater than 5,000 cps for a 25 wt-% solution of polymer and toluene at 20° C., or greater than about 10,000 cps, or even greater than about 15,000, or even about 20,000 cps or greater.

The hot melt adhesive composition may include at least one adhesive tackifier. As used herein, the term "tackifier" or "tackifying resin" includes any of the compositions described herein that are useful to impart tack to the hot melt adhesive composition. ASTM D-1878-61T defines tack as "the property of a material which enables it to form a bond of measurable strength immediately on contact with another surface." Typically the amount of tackifying resin ranges from about 40 wt-% to about 80 wt-% of the total weight of the adhesive. In order to minimize the plasticizing oil concentration, the adhesive composition may include at least about 50 wt-%, or at least about 60 wt-%, or even about 70 wt-% tackifying resin.

In general terms, useful tackifying resins useful in adhesives may include resins derived from renewable resources such as rosin derivatives including wood rosin, tall oil, gum rosin as well as rosin esters and natural and synthetic terpenes, and derivatives of such. Aliphatic, aromatic or mixed aliphatic-aromatic petroleum based tackifiers may also be useful. Representative examples of useful hydrocarbon resins includes α-methyl styrene resins, branched and unbranched C5 resins, C9 resins, resins based on dicyclopentadiene (DCPD), indene, piperylene, isobutylene and/or 1 butene, as well as styrenic and hydrogenated modifications of such. Tackifying resins range from being a liquid at about 25° C. (room temperature) to having a ring and ball softening point up to about 150° C. It may be preferred that the tackifier or tackifier mixture has a softening point of greater than about 80° C., more preferably about 100° C. or higher.

It may be preferred that a predominant amount of the tackifier is what is commonly known as a mid-block tackifying resin. In the case of block copolymers having unsaturated midblocks such as isoprene, a suitable tackifying resin is a hydrogenated DCPD or C9 resin; whereas for block copolymers having unsaturated butadiene midblocks, rosin derivatives such as rosin esters and hydrogenated styrenated terpene resins may be suitable.

The adhesive composition used may optionally include a plasticizing liquid in an amount up to about 10 wt-%. For purposes herein, a "plasticizer" or "plasticizing" liquid includes a flowable diluent having a molecular weight (Mw) of less than 3000, preferably less than 2000, and more preferably less than 1000 g/mol, which can be added to thermoplastics, rubbers and other resins to improve extrudability, flexibility, workability, or stretchability. A small amount of plasticizing oil may be preferred to soften the adhesive, improving its elasticity and extensibility. Block copolymer compositions having higher concentrations of plasticizing oil have been found to exhibit diminished bond strength when employed to bond lotion coated substrates, consistent with the teaching of the previously cited art references. It is believed that a hot melt adhesive composition as described herein is not resistant to oil-based skin care products such as lotions in the traditional sense, wherein the composition does not absorb or become plasticized by oil. Rather, the compositions are believed to be "robust" with respect to oil absorption, meaning that the composition is surmised to absorb oil to some extent, yet the absorption of oil does not detrimentally affect the adhesive properties.

Plasticizing oils are primarily hydrocarbon oils which are low in aromatic content and which are paraffinic or naphthenic in character. It may be preferred that plasticizing oils selected have low volatility, are transparent, and have as little color and odor as possible. The use of plasticizing liquids contemplated herein includes the use of liquid resins, olefin oligomers, liquid elastomer, low molecular weight polymers, vegetable oils and other natural oils as well as similar plasticizing liquids.

In the case of construction adhesives, solid plasticizers such as cyclohexane dimethanol dibenzoate and phthalate esters, may optionally be employed at amounts ranging up to about 40 wt-% or even at amounts ranging from about 10 wt-% to about 20 wt-%. However, in the case of elastic attachment adhesives, solid plasticizers tend to be avoided, since their presence reduces the rate of set. In the absence of a fast rate of set, elastomeric substrate that have been extended have the opportunity to relax prior to solidification of the adhesive. Further, as is known in the art, various other components can be added to modify the tack, color, odor, etc., of a hot melt adhesive. Additives such as antioxidants (for example, hindered phenolics (for example, IRGANOX 1010 and IRGANOX 1076 (BASF, Florham Park, N.J.—North American headquarters)), phosphites (for example, IRGAFOS 168 (BASF, Florham Park, N.J.—North American headquarters)), antiblock additives, pigments, and fillers, can also be included in the formulations.

The finished adhesive is typically light in color, having a molten Gardner color of less than about 6 or even less than about 4. It may be preferred that the viscosity is less than 30,000 cPs at 350° F. or more particularly, ranges from about 3,000 to about 15,000 cPs. Particularly for elastic attachment, the adhesive may have a ring and ball softening point of at least 190° F., or greater than 200° F.

Other potentially suitable block copolymer-based adhesives are described in U.S. Pat. No. 6,531,544, the disclosure of which is incorporated herein by reference in its entirety.

Adhesives Including Olefin Polymers

In other embodiments, useful adhesives may include at least one homogeneous ethylene/α-olefin interpolymer which is an interpolymer of ethylene and at least one C3-C20 α-olefin. The term "interpolymer" is used herein to indicate a copolymer, or a terpolymer, or a higher order polymer. That is, at least one other comonomer is polymerized with ethylene to make the interpolymer.

The homogeneous ethylene/α-olefin interpolymer is a homogeneous linear or substantially linear ethylene/α-olefin interpolymer. By the term "homogenous", it is meant that any comonomer is randomly distributed within a given interpolymer molecule and substantially all of the interpolymer molecules have the same ethylene/comonomer ratio within that interpolymer. The melting peak of homogeneous linear and substantially linear ethylene polymers, as obtained using differential scanning calorimetry, will broaden as the density decreases and/or as the number average molecular weight decreases. However, unlike heterogeneous polymers, when a homogeneous polymer has a melting peak greater than 115° C. (such as is the case of polymers having a density greater than 0.940 g/cm$^3$), it does not additionally have a distinct lower temperature melting peak.

In addition or in the alternative, the homogeneity of the polymer may be described by the SCBDI (Short Chain Branching Distribution Index) or CDBI (Composition Distribution Breadth Index), which are defined as the weight percent of the polymer molecules having a conomomer content within 50 percent of the median total molar comonomer content. The SCBDI of a polymer is readily calculated from data obtained from techniques known in the art, such as, for example, temperature rising elution fractionation (abbreviated herein as "TREF"), which is described, for example, in Wild et al., Journal of Polymer Science, Poly. Phys. Ed., Vol. 20, p. 441 (1982), in U.S. Pat. No. 4,798,081 (Hazlitt et al.), or in U.S. Pat. No. 5,089,321 (Chum et al.). It may be preferred that the SCBDI or CDBI for useful homogeneous ethylene/α-olefin interpolymers is greater than 50 percent, or greater than 70 percent, with SCBDI's and CDBI of greater than 90 percent being easily attained.

Useful homogeneous ethylene/α-olefin interpolymers may be characterized as having a narrow molecular weight distribution (Mw/Mn). For useful homogeneous ethylene/α-olefins, the Mw/Mn is from 1.5 to 2.5, or from 1.8 to 2.2, or even about 2.0.

A first polymer may be an interpolymer of ethylene with at least one comonomer selected from the group consisting of C3-C20 α-olefins, non-conjugated dienes, and cycloalkenes. Exemplary C3-C20 α-olefins include propylene, isobutylene, 1-butene, 1-hexene, 4-methyl-1-pentene, 1-heptene, and 1-octene. Suitable C3-C20 α-olefins may include 1-butene, 1-hexene, 4-methyl-1-pentene, 1-heptene, and 1-octene, or 1-hexene and 1-octene. Exemplary cycloalkenes include cyclopentene, cyclohexene, and cyclooctene. The non-conjugated dienes suitable as comonomers, particularly in the making of ethylene/α-olefin/diene terpolymers, are typically non-conjugated dienes having from 6 to 15 carbon atoms. Representative examples of suitable non-conjugated dienes include:
  (a) Straight chain acyclic dienes such as 1,4-hexadiene; 1,5-heptadiene; and 1,6-octadiene;
  (b) Branched chain acyclic dienes such as 5-methyl-1,4-hexadiene; 3,7-dimethyl-1,6-octadiene; and 3,7-dimethyl-1,7-octadiene;
  (c) Single ring alicyclic dienes such as 4-vinylcyclohexene; 1-allyl-4-isopropylidene cyclohexane; 3-allylcyclopentene; 4-allylcyclohexene; and 1-isopropenyl-4-butenylcyclohexene;
  (d) Multi-ring alicyclic fused and bridged ring dienes such as dicyclopentadiene; alkenyl, alkylidene, cycloalkenyl, and cycloalkylidene norbornenes, such as 5-methylene-2-norbornene; 5-methylene-6-methyl-2-norbornene; 5-methylene-6,6-dimethyl-2-norbornene; 5-propenyl-2-norbornene; 5-(3-cyclopentenyl)-2-norbornene; 5-ethylidene-2-norbornene; and 5-cyclohexylidene-2-norbornene.

One suitable conjugated diene is piperylene. Suitable dienes may be selected from the group consisting of 1,4-hexadiene; dicyclopentadiene; 5-ethylidene-2-norbornene; 5-methylene-2-norbornene; 7-methyl-1,6 octadiene; piperylene; and 4-vinylcyclohexene.

The molecular weight of the ethylene/α-olefin interpolymer will be selected on the basis of the desired performance attributes of the adhesive formulation. It may be preferred, however, that the ethylene/α-olefin interpolymer have a number average molecular weight of at least 3,000, preferably at least 5,000. It may be preferred that the ethylene/α-olefin interpolymer have a number average molecular weight of no more than 100,000, or no more than 60,000, or even less than 40,000.

When the ethylene/α-olefin interpolymer has an ultra-low molecular weight, and the like, a number average molecular weight less than 11,000, the ethylene/α-olefin interpolymer leads to a low polymer and formulation viscosity but is characterized by a peak crystallization temperature which is greater than that of corresponding higher molecular weight materials of the same density. In pressure sensitive adhesive applications, the increase in peak crystallization temperature translates to an increased heat resistance. Ultra-low molecular weight ethylene/α-olefin interpolymers are more fully described below.

The density of the ethylene/α-olefin interpolymer will likewise be selected on the basis of the desired performance attributes of the adhesive formulation. It may be preferred, however, that the ethylene/α-olefin interpolymer have a density of at least 0.850 g/cm$^3$, or at least 0.860, or even at least 0.870 g/cm$^3$. It may be preferred that the ethylene/α-olefin interpolymer have a density of no more than 0.965 g/cm$^3$, or no more than 0.900 g/cm$^3$, or no more than 0.890 g/cm$^3$, or even no more than 0.880 g/cm$^3$, or even no more than 0.875 g/cm$^3$.

The ethylene/α-olefin interpolymer may be present in suitable adhesives in an amount greater than 5, or even greater than 10 weight percent. The ethylene/α-olefin interpolymer may generally be present in the suitable adhesive in an amount of not more than 95, or not more than 80, or even not more than 70 weight percent.

The adhesive may include a single homogeneous ethylene/α-olefin interpolymer. In such an embodiment, the suitable homogeneous ethylene/α-olefin interpolymer may have a density ranging from 0.865 g/cm$^3$ to 0.885 g/cm$^3$. When it is desired to prepare an adhesive formulation with a minimal concentration of the homogeneous linear or substantially linear interpolymer, and the like, adhesive formulations containing less than 30 weight percent, or less than 25 weight percent of the homogeneous ethylene/α-olefin interpolymer, the melt index (12 at 190° C.) of the homogeneous linear or substantially linear interpolymer may be 50 or less, or 30 or less, and or even less than 10 g/10 min. It is believed that adhesive compositions including as little as 5 weight percent of the homogeneous ethylene/α-olefin interpolymer having a melt index less than 0.5 g/10 min. would yield an advantageous performance.

In the case of pressure sensitive adhesives, adhesives may include from 5 to 45 weight percent, or from 10 to 30, or even from 15 to 25 weight percent of a single homogeneous ethylene/α-olefin interpolymer. For other applications, the homogeneous linear or substantially linear interpolymer may be employed at concentrations greater than 30 weight percent and have a melt index of 500 g/10 min or less.

In another embodiment, the first homogeneous ethylene/α-olefin interpolymer may be blended with a second homogeneous ethylene/α-olefin interpolymer, wherein the first and second interpolymers differ in number average molecular weight by at least 5000, or at least 10,000, or even at least 20,000. In this embodiment, the combination of the lower molecular weight and higher molecular weight components will tend to yield an intermediate storage modulus at 25° C. and an improved probe tack.

In addition or in the alternative, the first homogeneous ethylene/α-olefin interpolymer may be blended with a second homogeneous ethylene/α-olefin interpolymer, wherein the first and second interpolymers differ in density by at least 0.005 g/cm$^3$, or even by at least 0.01 g/cm$^3$. In this embodiment, particularly in the case of pressure sensitive adhesives, as the density differential increases, the relative proportion of the higher density interpolymer will typically decrease, as the increased levels of crystallinity would otherwise tend to decrease storage modulus at 25° C. and probe tack to levels which would render them unsuitable for use as pressure sensitive adhesives.

In a particular embodiment, the adhesive may include a blend of two homogeneous ethylene/α-olefin interpolymers, the first interpolymer having a density of 0.870 g/cm$^3$ or less and the second interpolymer having density greater than 0.900 g/cm$^3$. When high cohesive strength is desired, the first and second homogeneous linear or substantially linear interpolymer, may both have relatively low melt indices, and the like, an 12 of less than 30 g/10 min. In contrast, for lower viscosity adhesive compositions, especially those which are sprayable at temperatures less than 325° F. (163° C.), the second homogeneous ethylene/α-olefin interpolymer will have a greater density than the first homogeneous ethylene/α-olefin interpolymer, and may have a melt index greater than 125, or greater than 500, or even greater than 1000 g/10 min.

Homogeneously branched linear ethylene/α-olefin interpolymers may be prepared using polymerization processes (for example, as described by Elston in U.S. Pat. No. 3,645,992) which provide a homogeneous short chain branching distribution. In his polymerization process, Elston uses soluble vanadium catalyst systems to make such polymers. However, others such as Mitsui Petrochemical Company and Exxon Chemical Company have used so-called single site catalyst systems to make polymers having a homogeneous linear structure. U.S. Pat. No. 4,937,299 to Ewen et al. and U.S. Pat. No. 5,218,071, to Tsutsui et al. disclose the use of catalyst systems based on hafnium for the preparation of homogeneous linear ethylene polymers. Homogeneous linear ethylene/α-olefin interpolymers are currently available from Mitsui Petrochemical Company under the trade name "Tafiner" and from Exxon Chemical Company under the trade name "Exact".

Substantially linear ethylene/α-olefin interpolymers are available from The Dow Chemical Company as Affinity (Registered Trademark) polyolefin plastomers and Engage (Registered Trademark) polyolefin elastomers. Substantially linear ethylene/α-olefin interpolymers may be prepared in accordance with the techniques described in U.S. Pat. No. 5,272,236 and in U.S. Pat. No. 5,278,272.

Other semicrystalline polymers that can be useful for adhesives are copolymers of propene with ethylene or alpha olefins comonomers where the crystallizable sequences are of the isopropylene type. The polymers most useful for adhesives have degree of crystallinity of 5-25%. Examples include VISTAMAXX (Exxon Mobil Corp., Irving, Tex.); VERSIFY (The Dow Chemical Company, Midland, Mich.); NOTIO (Mitsui Chemicals America, Inc., Rye Brook, N.Y.), and the like.

Modifying Polymers

Depending on the intended end use for the adhesive, it is often desirable to add at least one compatible polymer in addition to the homogeneous ethylene/α-olefin interpolymer at concentrations up to 25 percent by weight to increase the cohesive strength, improve the sprayability, modify the open time, increase the flexibility, etc. This modifying polymer may be any compatible elastomer, such as a thermoplastic block copolymer, a polyamide, an amorphous or crystalline polyolefin such as polypropylene, polybutylene or polyethylene wherein Mw is greater than 3000; an ethylenic copolymer such as ethylene-vinyl acetate (EVA), ethylene-methyl acrylate, or a mixture thereof. Surprisingly, the homogeneous ethylene/α-olefin interpolymers are also compatible with polyamides, resulting in plasticizer resistant pressure sensitive adhesives. The modifying polymer will typically be used in a relatively low concentration, so as not to detract from the improved properties of the homogeneous ethylene/α-olefin interpolymer. A suitable modifying polymer for increasing the open time and heat resistance may be polybutene-1 copolymer such as Duraflex (Registered Trademark) 8910 (Shell).

Interpolymers of ethylene are those polymers having at least one comonomer selected from the group consisting of vinyl esters of a saturated carboxylic acid wherein the acid moiety has up to 4 carbon atoms, unsaturated mono- or dicarboxylic acids of 3 to 5 carbon atoms, a salt of the unsaturated acid, esters of the unsaturated acid derived from an alcohol having 1 to 8 carbon atoms, and mixtures thereof. Terpolymers of ethylene and these comonomers are also suitable. Ionomers, which are completely or partially neutralized copolymers of ethylene and the acids described above, are discussed in more detail in U.S. Pat. No. 3,264,272. In addition, terpolymers of ethylene/vinyl acetate/carbon monoxide or ethylene/methyl acrylate/carbon monoxide containing up to 15 weight percent carbon monoxide may also be employed.

The ethylene to unsaturated carboxylic comonomer weight ratio may be from 95:5 to 40:60, or from 90:10 to 45:50, or even from 85:15 to 60:40. The melt index (12 at 190° C.) of these modifying interpolymers of ethylene may range from 0.1 to 150, or from 0.3 to 50, or even from 0.7 to 10 g/10 min. Physical properties, principally elongation, are known to decline to lower levels when the ethylene copolymer melt index is above 30 g/10 min.

Suitable ethylene/unsaturated carboxylic acid, salt and ester interpolymers include ethylene/vinyl acetate (EVA) including, but not limited to, the stabilized EVA described in U.S. Pat. No. 5,096,955, incorporated herein by reference; ethylene/acrylic acid (EEA) and its ionomers; ethylene/methacrylic acid and its ionomers; ethylene/methyl acrylate; ethylene/ethyl acrylate; ethylene/isobutyl acrylate; ethylene/n-butyl acrylate; ethylene/isobutyl acrylate/methacrylic acid and its ionomers; ethylene/n-butyl acrylate/methacrylic acid and its ionomers; ethylene/isobutyl acrylate/acrylic acid and its ionomers; ethylene/n-butyl acrylate/acrylic acid and its ionomers; ethylene/methyl methacrylate; ethylene/vinyl acetate/methacrylic acid and its ionomers; ethylene/vinyl acetate/acrylic acid and its ionomers; ethylene/vinyl acetate/carbon monoxide; ethylene/methacrylate/carbon monoxide; ethylene/n-butyl acrylate/carbon monoxide; ethylene/isobutyl acrylate/carbon monoxide; ethylene/vinyl acetate/monoethyl maleate; and ethylene/methyl acrylate/monoethyl maleate. Particularly suitable copolymers are EVA; EAA; ethylene/methyl acrylate; ethylene/isobutyl acrylate; and ethylene/methyl methacrylate copolymers and mixtures thereof. Certain properties, such as tensile elongation, are taught to be improved by certain combinations of these ethylene interpolymers, as described in U.S. Pat. No. 4,379,190. The procedures for making these ethylene interpolymers are well known in the art and many are commercially available.

Tackifier

A suitable adhesive may include from 0 to 95 weight percent of a tackifying resin. Typically, and particularly when it is desired to employ less than 30 weight percent of the homogeneous ethylene/α-olefin interpolymer, the adhesives may include from 10 to 75 weight percent, or from 20 to 60 weight percent tackifier.

In the alternative, in cases where it is desirable to employ at least 30 weight percent of the homogeneous ethylene/α-olefin interpolymer, adhesive formulations which contain minimal tackifier, and the like, less than 30 weight percent tackifier, or less than 25 weight percent tackifier, or even less than 20 weight percent tackifier, or even less than 15 weight percent tackifier, may be advantageous. In such applications, the homogeneous ethylene/α-olefin interpolymer may be provided as a blend with a second homogeneous ethylene/α-olefin interpolymer. In such instances, adhesives containing less than 10 weight percent tackifier, and even adhesives having no tackifier, may exhibit adequate tack.

In general terms, useful tackifying resins may include resins derived from renewable resources such as rosin derivatives including wood rosin, tall oil, gum rosin; rosin esters, natural and synthetic terpenes, and derivatives of such. Aliphatic, aromatic or mixed aliphatic-aromatic petroleum based tackifiers may also be useful in suitable adhesives. Representative examples of useful hydrocarbon resins includes α-methyl styrene resins, branched and unbranched C5 resins, C9 resins, C10 resins, as well as styrenic and hydrogenated modifications of such. Tackifying resins range from being a liquid at 37° C. to having a ring and ball softening point of about 135° C. Solid tackifying resins with a softening point greater than about 100° C., or with a softening point greater than about 130° C. may be useful to improve the cohesive strength of suitable adhesives, particularly when only a single homogeneous ethylene/α-olefin interpolymer is utilized.

For suitable adhesives, a suitable tackifying resin may be predominantly aliphatic. However, tackifying resins with increasing aromatic character may also be useful, particularly when a second tackifier or mutually compatible plasticizer is employed.

Plasticizer

In particular embodiments, the plasticizer may be provided to the adhesive in amounts up to 90 weight percent, preferably less than 30 weight percent, and still more preferably less than about 15 weight percent of the adhesive. The plasticizer may be either a liquid or a solid at ambient temperature. Exemplary liquid plasticizers include hydrocarbon oils, polybutene, liquid tackifying resins, and liquid elastomers. Plasticizer oils are primarily hydrocarbon oils which are low in aromatic content and which are paraffinic or napthenic in character. Plasticizer oils are preferably low in volatility, transparent and have as little color and odor as possible. The use of plasticizers also may include the use of olefin oligomers, low molecular weight polymers, vegetable oils and their derivatives and similar plasticizing liquids.

When a solid plasticizing agent is employed, it may be desired that the agent have a softening point above 60° C. It is believed that by combining the homogeneous ethylene/α-olefin interpolymer with a suitable tackifying resin and a solid plasticizer such as a cyclohexane dimethanol dibenzoate plasticizer, the resulting adhesive composition may be applied at temperatures below 120° C., or even below 100° C. Although a 1,4-cyclohexane dimethanol dibenzoate compound commercially available from Velsicol under the trade name Benzoflex (Registered Trademark) 352 is exemplified, any solid plasticizer that will subsequently recrystallize in the compounded thermoplastic composition is suitable. Other plasticizers that may be suitable for this purpose are described in EP 0422 108 B1 and EP 0 410 412 B1, both assigned to H.B. Fuller Company.

Waxes

Waxes may be usefully employed in suitable adhesive compositions, particularly when the adhesive composition is intended to be relatively tack free upon cooling and solidifying, such as for various packaging and bookbinding applications as well as foam in place gaskets. Waxes are commonly used to modify the viscosity and reduce tack at concentrations up to 60 percent by weight, or even less than about 25 percent by weight. Useful waxes may include paraffin waxes, microcrystalline waxes, Fischer-Tropsch, polyethylene and by-products of polyethylene wherein Mw is less than 3000. It may be desired that the concentration of wax be less than 35 percent by weight for high melt point waxes. At wax concentrations above 35 percent by weight, paraffin waxes may be used.

Also suitable are ultra-low molecular weight ethylene/α-olefin interpolymers prepared using a constrained geometry catalyst, and may be referred to as homogeneous waxes. Such homogeneous waxes, as well as processes for preparing such homogeneous waxes, are set forth in the Examples below. Homogeneous waxes, in contrast to paraffinic waxes and crystalline ethylene homopolymer or interpolymer waxes, will have a Mw/Mn of from 1.5 to 2.5, or even from 1.8 to 2.2.

Homogeneous waxes will be either ethylene homopolymers or interpolymers of ethylene and a C3-C20 α-olefin. The homogeneous wax will have a number average molecular weight less than 6000, or even less than 5000. Such homogeneous waxes may have a number average molecular weight of at least 800, or even at least 1300.

Homogeneous waxes lead to a low polymer and formulation viscosity, but are characterized by peak crystallization temperatures which are greater than the peak crystallization temperatures of corresponding higher molecular weight materials of the same density. In adhesive applications, the increase in peak crystallization temperature translates to an increased heat resistance, and the like, improved creep resistance in pressure sensitive adhesives, and improved SAFT in hot melt adhesives.

Other Additives

As is known in the art, various other components can be added to modify the tack, color, odor, etc., of a hot melt adhesive. Additives such as antioxidants (for example, hindered phenolics (for example, IRGANOX 1010 and IRGANOX 1076), phosphites (for example, IRGAFOS 168)), antiblock additives, pigments, and fillers, can also be included in the formulations. It may be preferred that the additives should be relatively inert and have negligible effects upon the properties contributed by the homogeneous linear or substantially linear interpolymer, tackifying agent, and plasticizing oil.

Other potentially suitable adhesives including olefin polymers are described in U.S. Pat. No. 7,199,180, the disclosure of which is incorporated herein by reference in its entirety.

Additional Examples

Additional examples of suitable adhesives are products designated H2861 and H20043F, products of Bostik S.A., Paris, France, and/or Bostik, Inc., Wauwatosa, Wis. Hot melt adhesives of a type deemed suitable for such use are typically mixtures of a high molecular weight polymer with lower molecular weight tackifiers and oils. A typical adhesive for this application might contain about 35% styrene-isoprene block copolymer with molecular weight of 80-250 kg/mol and 65% additives with molecular weights in the range of 0.5-3 kg/mol.

Advantageous Formulations for Elastic Films Used with Particular Adhesives

Low molecular weight species of, e.g., plasticizers included in some adhesives can be quite mobile at temperatures above the glass transition temperature of the mixture in which they reside. For example, in an adhesive formed of a mixture of components of the type contemplated herein, a high molecular weight polymer component may have a glass transition temperature Tg of, for example, about −50° C., while a lower molecular weight component may have a glass transition temperature Tg of, for example, about 80° C.; and the Tg for the mixture may be, for example, about 15° C. In such an example, the low molecular weight components can be relatively mobile at temperatures above 15° C. At room or body temperature, typical diffusion coefficients (The Mathematics of Diffusion, John Crank, Oxford University Press, USA ISBN-10: 0198534116) for these low molecular weight species in polymers like these are on the order of $10^{-13}$ m$^2$/s.

As a consequence of this mobility, when these adhesives come into contact with a second material (e.g., an elastomeric film) the low molecular weight species can diffuse into the second material if they are soluble in the polymer(s) forming the second material. Conversely, if the second material contains low molecular weight species such as plasticizers, those may also diffuse into the adhesive, by the same mechanism. Without intending to be bound by theory, it is believed that either type of diffusion can decrease adhesive strength by two distinct mechanisms.

First, it may change the adhesive's composition. It is believed that this effect is more likely when elastomers with relatively high contents of oil are used. Diffusion of the oil into the adhesive material may cause unwanted plasticization of the end blocks of the adhesive polymer(s).

Second, the adhesive can lose mass if more material diffuses out than in, similar to the "moving marker" diffusion experiments known in the literature (see, for example, E. J. Kramer, P. Green and C. J. Palmstrom, Polymer (vol. 25, pp. 473-480) (1984). This effectively decreases the quantity of adhesive material present, which generally corresponds with decreased adhesion between the components joined.

Following experimentation, it is believed that replacing some of the elastomeric film's plasticizer with a tackifier as defined herein such as/or a tackifying resin as produced and sold by Eastman Chemical Company, Kingsport, Tenn. under the trademarks/trade names REGALREZ, REGALITE and EASTOTAC; Exxon Mobil Corp./ExxonMobil Chemical, Houston, Tex. under the trademark/trade name ESCOREZ; and Arakawa Europe GmbH, Schwalbach, Germany under the trademark/trade name ARKON, and the like, may address and reduce the effects of one or both mechanisms.

A suitable tackifier for this purpose may have a ring-and-ball softening point from 80° C. to 150° C., more preferably from 90° C. to 145° C., or even more preferably from 100° C. to 140° C.; a glass transition temperature Tg (midpoint) from 0° C. to 100° C., molecular weight Mn from 500 g/mol to 2000 g/mol.

Table 5 shows the weight percent of components in formulas for making several control and modified film Samples. The 54033 is a hydrogenated SEEPS block copolymer available from Kuraray America, Inc. in Pasadena, Tex. 54033 is a known SEEPS block copolymer. The oil in Table 5 is a white mineral oil such as DRAKEOL 600 (Calumet Specialty Prods. Partners, L.P., Indianapolis, Ind.); HYDROBRITE 550 (Sonneborn Refined Products, Parsippany, N.J.), or KRYSTOL 550 (Petro-Canada Lubricants, Inc., Mississauga, Ontario, Canada). REGALREZ 1126 and REGALITE 1125 are tackifiers available from Eastman Chemical Company in Kingsport, Tenn. The PS 3190 is a polystyrene homopolymer available from NOVA Chemical Company, Canada. ARKON P-140 is a tackifier available from Arakawa Europe GmbH, Schwalbach, Germany.

Samples 16 and 17 were the control samples. For Samples 18-21 (modified samples), it can be seen in Table 5 that one of various tackifiers (REGALREZ 1126, REGALITE 1125 or ARKON P-140) were substituted for a portion of the oil in Samples 16 and 17.

Samples 16-21 are produced by extruding a thermoplastic composition through a slot die to form a film that is 100 mm wide and 100 μm thick. The thermoplastic composition is formed by extruding material in a Leistritz (27 mm) twin screw extruder with extended mixing sections. First, the oil and SEEPS block copolymer are mixed together, and then the polystyrene and tackifier (when used) are blended into the mixture, which is then fed into the extruder. Temperatures in the extruder typically range from 170-230° C. Subsequently, the compositions are formed into films using a ThermoFisher 20 mm single screw extruder. Temperatures in the ThermoFisher extruder typically range from 170-230° C.

TABLE 5

| | | Sample No. | | | | | |
| --- | --- | --- | --- | --- | --- | --- | --- |
| Film Components | Adhesive | 16 Wt. % | 17 Wt. % | 18 Wt. % | 19 Wt. % | 20 Wt. % | 21 Wt. % |
| S4033 | | 56 | 66 | 56 | 56 | 56 | 60 |
| PS 3190 | | 14 | 16.5 | 14 | 14 | 14 | 10 |
| Oil | | 30 | 17.5 | 15 | 15 | 15 | 20 |
| REGALREZ 1126 | | | | 15 | | | |
| REGALITE 1125 | | | | | 15 | | 10 |
| ARKON P-140 | | | | | | 15 | |
| Slow Peel Test (μm/sec) | H2861 | 4.4 | 0.92 | 1.8 | 1.3 | 0.82 | 3.4 |
| | H20043F | 3.4 | 2.9 | 0.25 | 0.2 | 0.028 | 1.1 |
| Peel Force Test (N/mm) | H2861 | 3.31 | 4.48 | 4.23 | 4.22 | 4.6 | 4.08 |
| | H20043F | 5.84 | 5.66 | 6.52 | 6.73 | 6.5 | 6.77 |

After the Samples shown in Table 5 were produced, specimens of them were prepared and subjected to the Slow Peel Test and the Peel Force Test described below, using two different adhesives. In the table, H2861 and H20043F are adhesive products of Bostik S.A., Paris France, and Bostik, Inc., Wauwatosa, Wis.

A lower value for Slow Peel is believed to indicate greater resistance to separation of an aged specimen under a fixed load over time, and therefore, generally, is believed to indicate a film-adhesive combination that performs relatively better after storage, and when placed under a sustained load over time (for example, a stretch laminate of an absorbent article, under strain during sustained wear of the article). From the data in Table 5, it can be seen that Samples 18-20 performed markedly better in this regard, than Samples 16 and 17. As noted, Samples 18-20 had tackifiers substituted for portions of the oil in Samples 16 and 17. The Bostic H20043F adhesive appeared to perform better with these modified films than the Bostic H2861 adhesive.

A greater value for Peel Force is believed to indicate greater resistance to separation to failure (increasing load), and therefore, a stronger initial adhesive bond of an aged specimen and greater ability to withstand temporary forces (such as in a stretch laminate of an absorbent article, during application in which the consumer stretches parts of the article, such as fastening members or ears, to apply it to a wearer). As can be seen in Table 5, some improvement was evident with the combination of Bostic H20043F and the modified films, but was relatively lacking with the combination of Bostic 2861 and the modified films. The Bostic H20043F exhibited superior adhesion, both with the modified films (Samples 18-21) and the control films (Samples 16 and 17).

The foregoing data suggest that, for maintenance of adhesive strength, an improved combination of film and adhesive includes a modified film (i.e., having tackifier substituted for oil), and may include particular adhesives such as Bostic H20043F adhesive and those having effectively comparable components and properties.

Article

In certain embodiments, the film and/or film containing laminate may be incorporated into an article (e.g., a diaper or training pant), where it is particularly important that the article function as intended for a predetermined amount of time. Thus, suitable time-to-fail values are important for providing an indication that an article or article component that includes the film is less likely to suffer catastrophic failure in use.

FIG. 1 shows an exemplary embodiment of a diaper 200 in a flat-out, uncontracted state (i.e., with no elastic induced contraction). Portions of FIG. 1 are cut away to more clearly show the construction of the diaper 200. The outer, garment-facing surface of the diaper 200 is oriented towards the viewer and the opposing inner, wearer-facing surface is oriented away from the viewer. The diaper 200 as shown in FIG. 1 has a longitudinal centerline 211 extending in the longitudinal direction and a lateral centerline 212 orthogonal thereto. The diaper 200 may include a first waist region 256, a second waist region 258, and a crotch region 257 disposed therebetween. As shown in FIG. 1, the diaper 200 may include a liquid pervious topsheet 230; a liquid impervious outer cover 220 joined with at least a portion of the topsheet 230, for example, along the periphery of the diaper 200; and an absorbent core assembly 240 positioned between the topsheet 230 and the outer cover 220. The inner, wearer-facing surface of the diaper 200 may include at least a portion of the topsheet 30 and other components, which may be joined to the topsheet 30. The outer, garment-facing surface may include at least a portion of the outer cover 220 and other components, which may be joined to the outer cover 220. The diaper 200 may include an elastic waist feature 260 and a fastening system. The fastening system may include an ear 265 joined to at least one of the front and back waist regions 256 and 258 and extending laterally outward therefrom. In certain embodiments, the ear 265 and one or both waist regions 256 and/or 258 may be formed from as a unitary structure, for example, by forming the two elements from the same substrate. The ear 265 may include a fastening tab 270, which extends laterally outwardly therefrom. The fastening tab 270 may include a fastening element that is engageable with another portion of the diaper 200. "Engageable" means one element is configured to be joined to another element, for example, through the creation of an entanglement-type mechanical bond. Nonlimiting examples of suitable absorbent articles for use with the tear resistant film disclosed herein may be found in U.S. Pat. Nos. 3,860,003; 4,808,178; 4,909,803; 5,151,092; 5,221,274; 5,554,145; 5,569,234; 5,580,411; 6,004,306; 7,626,073; U.S. Publication No. 2007/0249254; and copending U.S. Ser. No. 13/026,563, titled "Absorbent Article With Tear Resistant Components, filed on Feb. 14, 2011 by Mansfield and further identified as P&G attorney Docket No. 11995.

Test Methods

General

Environmental conditions for the test methods herein include a temperature of 23° C.±2° C., unless indicated otherwise. In some instances, the sample to be tested may include one or more layers of material in addition to the film material (e.g., samples taken from commercially available articles). In such instances, the film is carefully separated from the other layers of material so that damage to the film is avoided. If the film is damaged (i.e., torn, cut, punctured, etc.) as a result of separating the film from the other material, the sample is discarded and another undamaged sample is obtained.

Hysteresis

Figure 10:
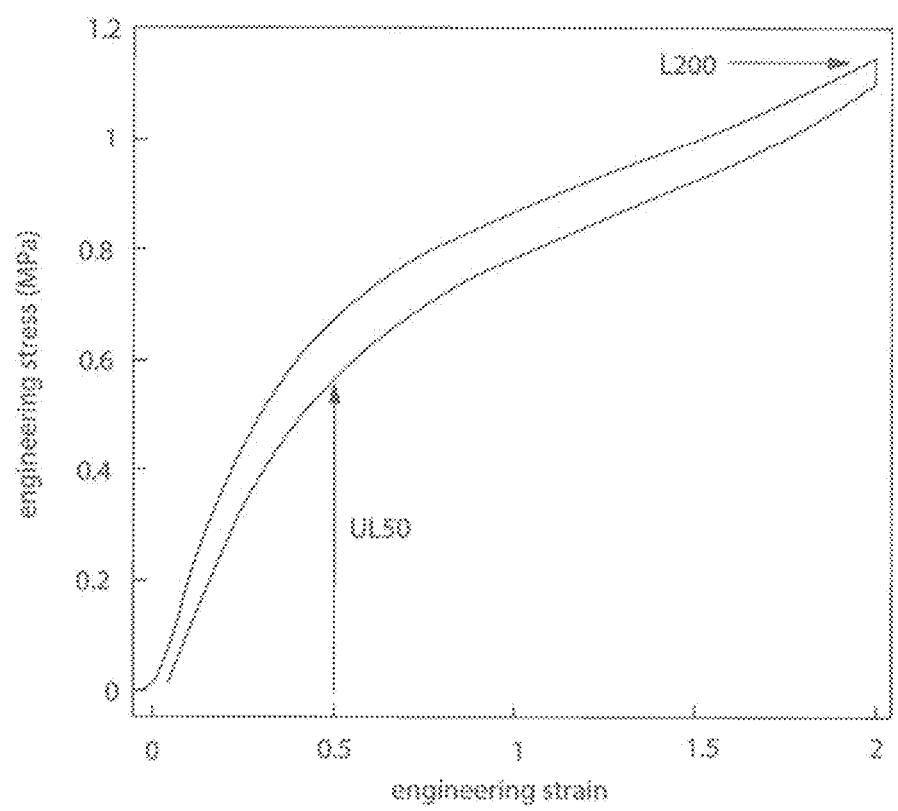
FIG. 10 is a chart illustrating an exemplary stress-strain curve generated during the Hysteresis Test.

The Hysteresis test is performed in accordance with ASTM D882-02 using line-contact grips and a load-hold-unload sequence, along with the exceptions and/or conditions set forth below. FIG. 10 is provided to illustrate the portion of the stress-strain curve that includes the L200 value (i.e., the engineering stress at 200% strain during loading) and the UL50 value (i.e., the engineering stress at 50% strain during unloading) generated during the Hysteresis test. One load-unload cycle is run.

specimen width: 25.4 mm
gauge length: 25.4 mm
testing speed: 4.233 mm/s
temperature: 22-24 C
applied displacement: 50.8 mm (200% engineering strain)
hold time at the applied displacement: 30 seconds
If grip design does not accommodate the 50 mm extra sample length indicated in section 6.1 of ASTM D882-02, prepare samples to a length that allows gripping the appropriate gauge length without interfering with other parts of the grip. In such cases care must be taken to mount the specimen with proper alignment, gripping and gauge definition.

The following are recorded:
engineering stress at 200% engineering strain during the load segment (L200)
engineering stress at 50% engineering strain during the load segment (UL50)
engineering strain during unloading where the force decreases below 0.05N (Ls).
Engineering Strain (e) is defined as $e = (L-L0)/L0 = z/L0$ where:
L0 is the gauge length (i.e., the distance between lines of grip contact when the undeformed sample is mounted in the grips. The L0 in the present example is 10 mm.
Grip position, L, is the distance between lines of grip contact during the tensile test.
Displacement, z, is defined as $z = L - L0$.

Engineering Strain Rate is the first time derivative of the Engineering Strain, expressed in units of s$^{-1}$. A convenient form for calculating Engineering Strain Rate is $$\frac{d\varepsilon}{dt} = \frac{v}{Lo}$$

where:

v and L0 are the speed at which one grip moves relative to the other, and the sample's gauge length respectively. Thus, the hysteris test applies an engineering strain rate of [(4.233 mm/s)/25.4 mm]=0.167 s$^{-1}$.

The set is then defined as Ls, expressed as a proportion of the engineering strain at applied displacement. For example if 200% engineering strain is applied to the sample and it goes slack at an engineering strain of 20% during unloading, the set is calculated as 20%/200%=0.10=10%.

When using the hysteresis test to determine whether a material meets the definition of "elastic" or "plastic" as described in the definitions, an applied displacement of 12.7 mm (i.e. an engineering strain of 50%) is used.

Basis Weight (Mass Per Unit Area)

The basis weight of each film is determined according to INDA Standard Test WSP 130.1 (09). All conditioning and testing is conducted in an atmosphere of 23±2° C., and 50±5% relative humidity.

The average of 5 specimens is reported as the Average Basis Weight in grams per square meter (gsm) to 3 significant digits. If the dimensions of the available material are smaller than indicated in the method, the best reasonable determination of the specimen's dimensions and mass is made.

Effective Average Thickness

The Effective Average Thickness of the film is calculated from the Average Basis Weight as follows.

Effective Average Thickness=Average Basis Weight/density

Units:

Thickness: micrometers (μm)

Basis Weight: gsm density=0.92 grams per cm$^3$ (g/cc)

Results are reported in microns (μm) to 3 significant digits.

Air Permeability Test

The air permeability of a substrate (e.g., film, laminate, or article component) is determined by measuring the flow rate of standard conditioned air through a test specimen driven by a specified pressure drop. This test is particularly suited to materials having relatively high permeability to gases, such as nonwovens, apertured films and the like. ASTM D737 is used, modified as follows.

A TexTest FX3300 instrument or equivalent is used, which are available from Textest AG, Switzerland, or from Advanced Testing Instruments ATI in Spartanburg S.C., USA. The procedures described in the Operating Instructions for the TEXTEST FX 3300 Air Permeability Tester manual for the Air Tightness Test and the Function and Calibration Check are followed. If a different instrument is used, similar provisions for air tightness and calibration are made according to the manufacturer's instructions.

The test pressure drop is set to 125 Pascal and the 5 cm$^2$ area test head (model FX3300-5) is used. After making the measurement of a specimen according to the procedure given in the Operating Instructions for the TEXTEST FX 3300 Air Permeability Tester manual, the result is recorded to three significant digits. The average of 5 specimens air permeability data of this sample (in m$^3$/m$^2$/min) is calculated and reported as the Air Permeability Value.

Differential Scanning calorimetry (DSC).

Figure 2:
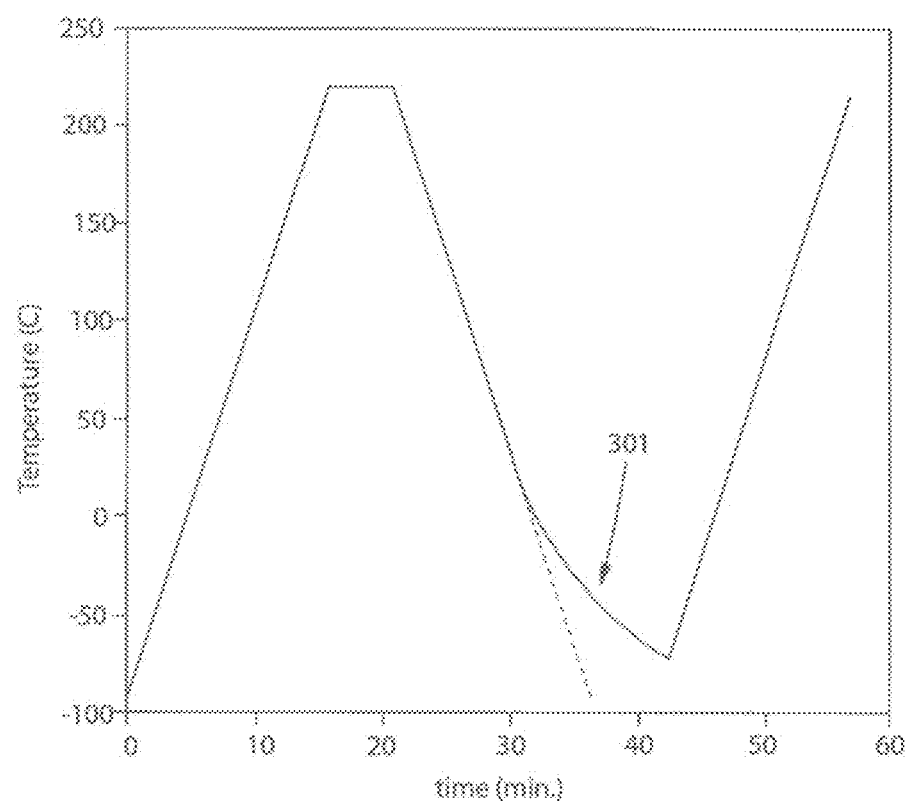
FIG. 2 is a chart of time versus temperature for use with the DSC test.

The DSC test is used to measure the melting temperature ($T_m$) of a polymer. The $T_m$ is determined by DSC measurements according to ASTM D3418-08 (note that $T_n$, is referred to as $T_{pn}$, in the ASTM method), except that the time-temperature profile shown in FIG. 2 is used for the measurement. Calibration is performed with a heating rate of 20° C./min. The temperature profile may include the non-linear portion 301 of profile at Time=30-42 minutes, as shown in FIG. 2. The non-linear portion 301 is a manifestation of limitations in the cooling capability of the apparatus. It is recognized that this deviation from the nominal cooling rate might have a modest effect on the observed melting curve, but all DSC data herein follow the same profile.

Slow Tear Test (Time-to-Fail)

The purpose of the Slow Tear Test is to measure the time-to-fail for a notched film sample. It is believed that the Slow Tear Test provides an indication of how well a film with tears, holes, or other defects resists propagation of the tear, hole, or defect, and in particular measures the time-to-fail for a notched film sample held at 37.8° C. and an engineering strain of 150%.

Setup

Gauge Length: 25.4 mm

Sample Width: 25.4 mm

Notch Length: 2 mm (single edge notch)

Testing Temperature: 37.8° C.

Applied engineering strain: 150% (i.e. apply and hold 38.1 mm of displacement.)

Figure 3:
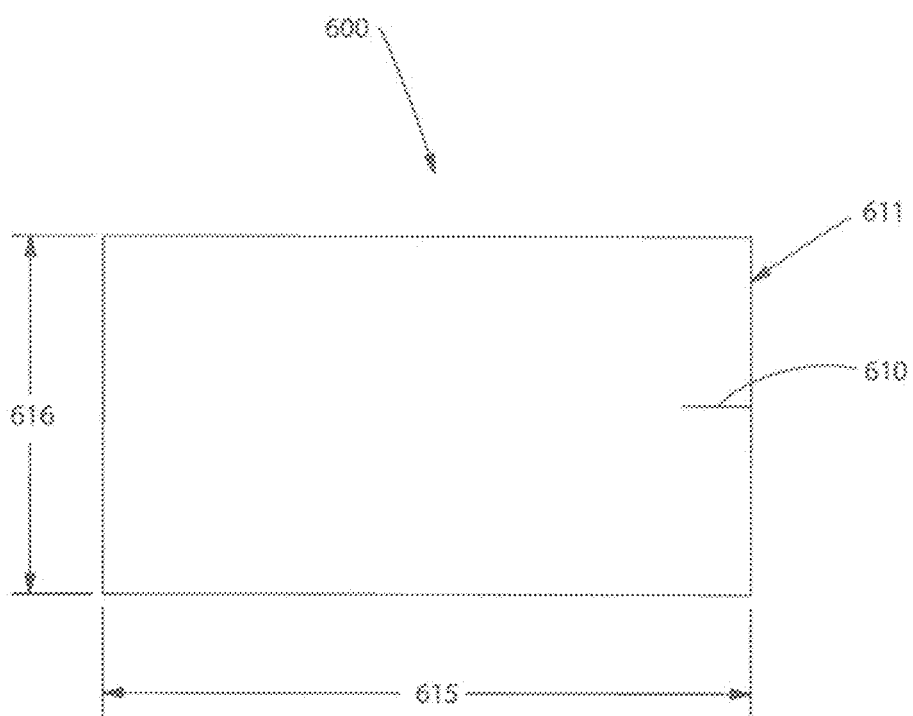
FIG. 3 is a side view of grip suitable for use with the Slow Tear Test.
Figure 5:
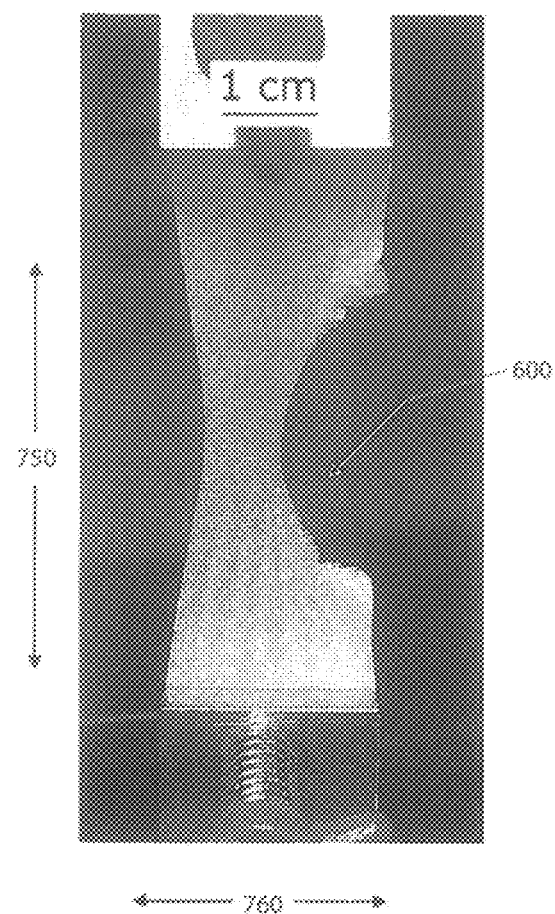
FIG. 5 shows a sample being subjected to the Slow Tear Test.

Direction of applied deformation: the same direction that the film would be strained during normal use of the article Sample Preparation FIG. 3 is provided to illustrate particular aspects of the sample preparation. On a cutting mat, the film material is sandwiched between sheets of photocopier paper. The top sheet of paper has lines printed on it to facilitate cutting the sample 600 to the correct dimensions and for correct notch 610 length. A sharp, X-ACTO brand knife and straight edge are used to prepare the samples 600. A sample 600 is cut such that it has a width 615 of 25.4 mm and a length 616 that is suitable for loading the sample into the grips and is sufficient to provide a gauge length of 25.4 mm without undesirably interfering with the test. A 2 mm notch 610 is cut extending inward from the side edge 611 of the sample 600 and perpendicular thereto. In this particular example, the width 615 and length 616 of the sample 600 coincide with the machine direction 750 and transverse direction 760, respectively, as shown in FIG. 5, such that the direction in which the sample is deformed is the transverse direction 760 during testing.

Grips

Figure 4:
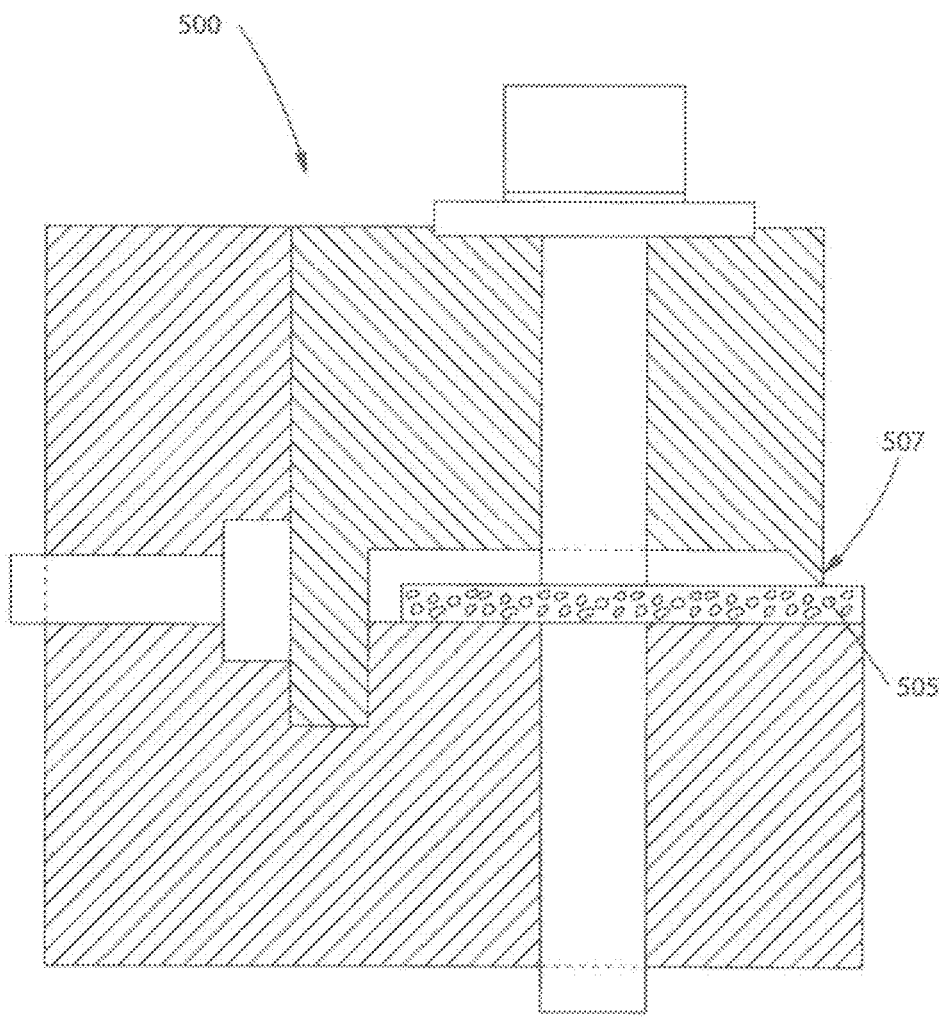
FIG. 4 is a plan view of notched sample for use in the Slow Tear Test.
Figure 6:
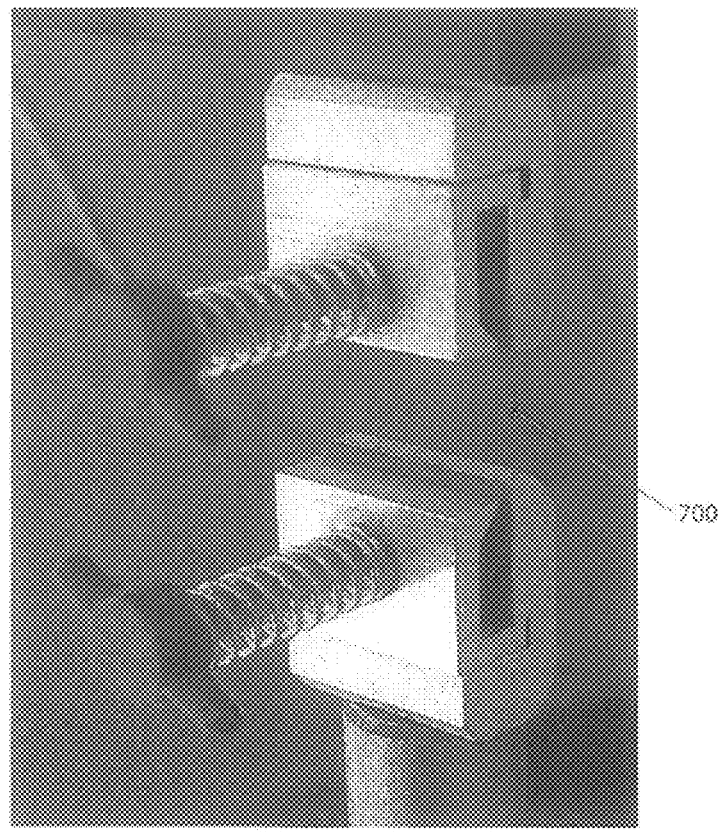
FIG. 6 shows a pair of opposing grips for use in the Slow Tear Test.

Line contact grips 500 of the type shown in FIG. 4 are used for this test. The line grips 500 are selected to provide a well-defined gauge and avoid undue slippage. The sample is positioned such that it has minimal slack and the notch is centered between the grips. The apexes 507 of the grips 500 are ground to give good gauge definition while avoiding damage or cutting of the sample. The apexes are ground to provide a radius in the range of 0.5-1.0 mm. A portion of one or both grips 500 may be configured to include a material 507 that reduces the tendency of a sample to slip, (e.g., a piece of urethane or neoprene rubber having a Shore A hardness of between 50 and 70). FIG. 6 shows a pair of opposing grips 700 suitable for use herein.

Apparatus

The grips are mounted in a frame (e.g., Chatillon Mont. 150L or similar) that allows hand-operated movement of one grip with respect to the other. Gauge blocks are used to establish precise grip positions for sample loading and sample testing. The entire frame is mounted in a chamber equipped with temperature control equipment well suited for maintaining the air temperature in the immediate proximity of the sample at 37.8° C.

Figure 7:
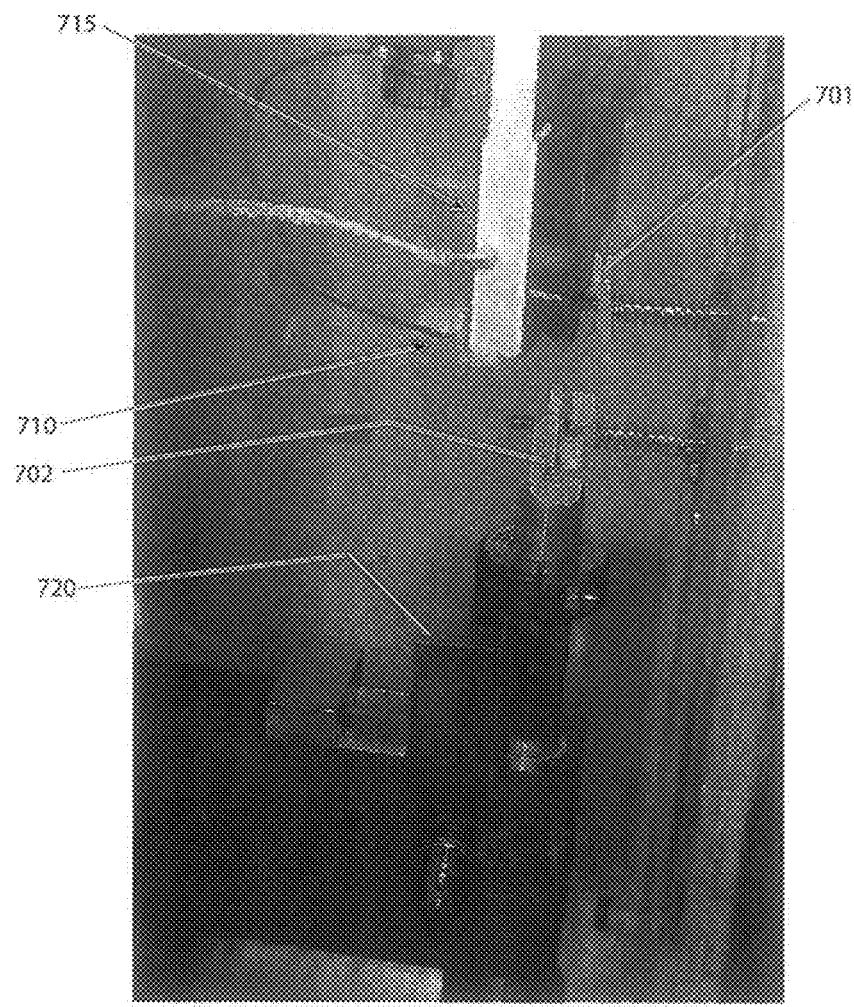
FIG. 7 shows an apparatus and set up for the Slow Tear Test.

FIG. 7 shows an exemplary apparatus 800 for conducting the Slow Tear Test. As shown in FIG. 7, the apparatus 800 is set up in a temperature control chamber and includes a top grip 701, a bottom grip 702, a gauge block 720 for precisely positioning at least the bottom grip 702, and a thermocouple 710 for monitoring the temperature in the chamber. A force transducer 715 is deployed in mechanical communication with the top grip 701. The force transducer 715 includes a suitable quality signal conditioner for enabling the desired force measurement without significant drift, noise, etc. The force transducer is selected to provide adequate resolution to identify when the final failure of a sample occurs. The output from the signal conditioner is connected to an analog-to-digital converter interfaced with a computer to allow data acquisition during the test. The force data are sampled at a frequency of at least one data point per second while the sample is being extended and during its initial force decay. The frequency of subsequent data sampling must be sufficient to determine the time-to-fail of a sample from the data to within 5% of the actual time-to-fail value of the sample. Time=0 is assigned to the first data point after the sample is extended 150% (i.e., 1 second after extension is complete).

Testing

Figure 8:
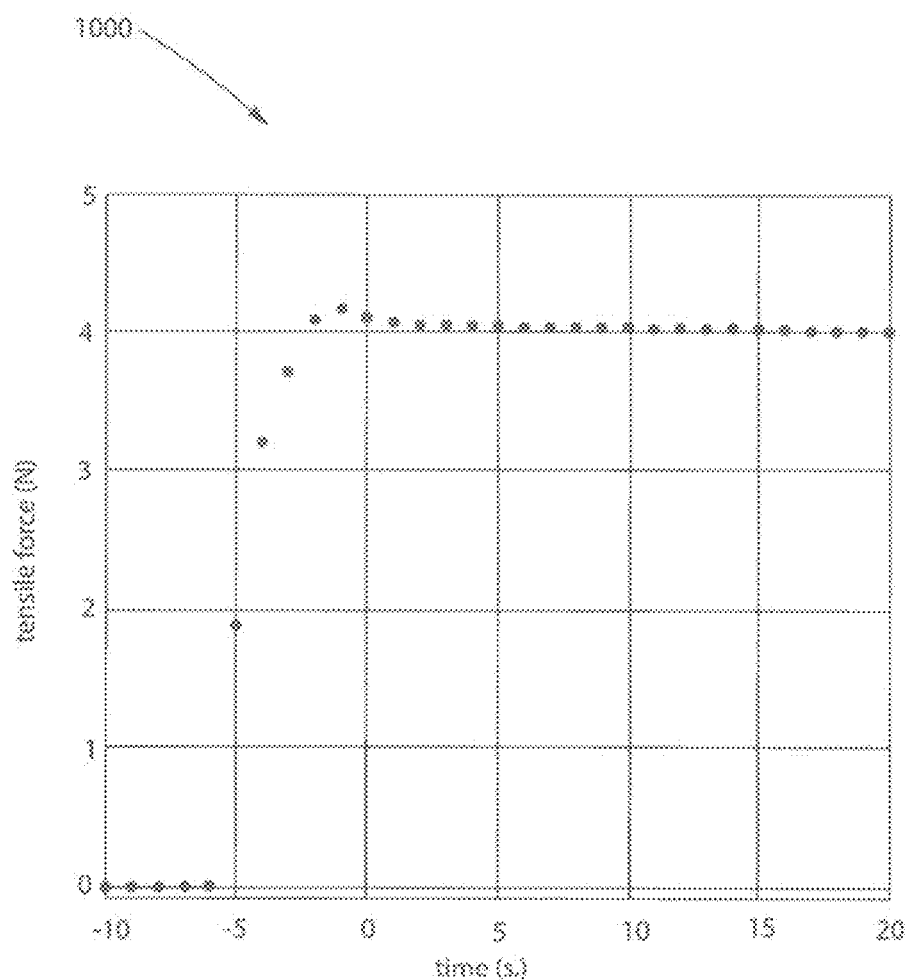
FIG. 8 is a chart of tensile force versus time for the Slow Tear Test.

The grip separation (i.e., gauge length) is set at 25.4 mm and the sample is inserted so that the grips form well-defined lines of contact on the sample. If surface tackiness makes it difficult to mount the sample then a powder such as corn starch may be used to mitigate tack. The grip bolts are tightened to provide a secure grip, but without cutting the sample. The temperature chamber door is closed to allow the temperature to equilibrate at target temperature for two minutes. Data acquisition is commenced. The desired displacement (38.1 mm) is applied to the sample over the course of 5 seconds as shown in FIG. 8 (i.e., from Time=−6 to Time=−1). FIG. 8 shows a chart 1000 illustrating the time versus force data that are collected during the test at one-second intervals. As used herein, "time-to-fail" means the time at which the sample breaks and the force reaches its unloaded baseline value.

High Speed Tensile Test

The High Speed Tensile Test is used to measure the Tensile Strength of a sample at a relatively high strain rate. The method uses a suitable tensile tester such as an MTS 810, available from MTS Systems Corp., Eden Prairie Minn., or equivalent, equipped with a servo-hydraulic actuator capable of speeds exceeding 5 m/s after 28 mm of travel, and approaching 6 m/s after 40 mm of travel. The tensile tester is fitted with a 50 lb. force transducer (e.g., available from Kistler North America, Amherst, N.Y. as product code 9712 B50 (50 lb)), and a signal conditioner with a dual mode amplifier (e.g., available from Kistler North America as product code 5010). Suitable grips such as those described above may be used to secure the samples during tensile testing.

Film samples having dimensions of 19 mm wide×16.5 mm long are prepared in the same manner described above for the Slow Tear Test. The mass of each sample measured is to within ±0.1 mg, and the length of each sample is measured to within ±0.1 mm. The tensile grips are moved to a grip separation of 10 millimeters (i.e. the distance between the lines of contact between sample and grip surface). The sample is mounted in the grips, optionally using powder such as corn starch (to kill the sample's tack, after sample has been weighed) and a thin piece of tape to help hold the sample straight and flat while mounting in grips (if used, tape must remain behind the lines of gripping so that it does not interfere with the sample's gauge during the test). The grips are moved close together to put as much slack as possible into the film sample without the grips interfering with one another. Actuator movement is selected such that the sample sees a grip speed of between 5 and 6 meters per second at break. Typically, during testing, one of the grips is kept stationary and the opposing grip is moved, but embodiments wherein both grips move are also contemplated herein.

Figure 9:
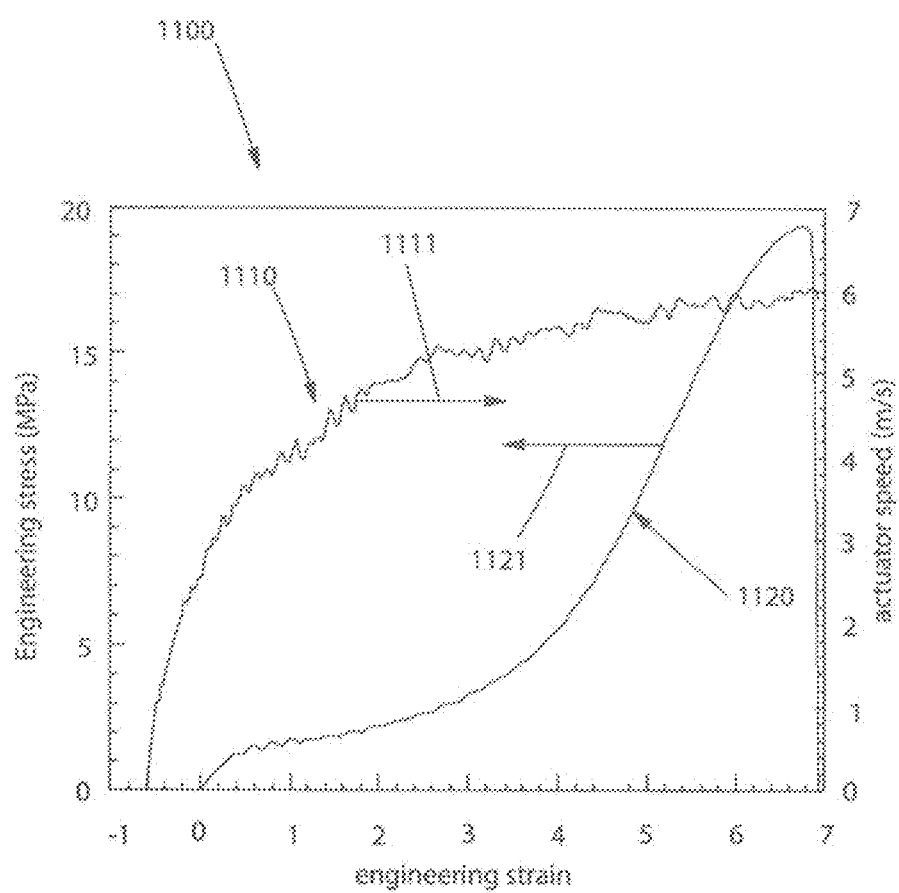
FIG. 9 is a chart of a suitable deformation regimen for the High Speed Tensile Test.

FIG. 9 illustrates a suitable, exemplary deformation regimen depicted as a chart 1100 with two curves 1110 and 1120. The first curve 1110 illustrates a plot of actuator speed (i.e., the relative speed at which one grip is moving away from the other grip) versus engineering strain. The arrow 1111 points to the y-axis used for this plot 1110. The second curve 1120 illustrates a plot of engineering stress versus engineering strain and uses the left-side y-axis, as indicated by the arrow 1121. The force and actuator displacement data generated during the test are recorded using a Nicolet Integra Model 10, 4 channel 1 Ms/s, 12 bit digitizer oscilloscope with the data acquisition frequency set at 40 kHz. The resulting force data may be expressed as Engineering Stress in megaPascals (MPa) using the following relationships.

Engineering Stress is defined as $$\sigma = 10^{-6} * \frac{F}{A}$$

where:
F is force in Newtons and
A is the cross-sectional area (m$^2$) of the sample, calculated as $$A = \frac{mass}{length * \rho}$$

where:
mass and length are measurements of the individual sample, as described above, and are expressed in kilograms and meters respectively.
ρ is the density of the sample, taken as 950 or 920 kg/m$^3$ for elastomers predominantly of non-hydrogenated or hydrogenated styrenic block copolymers, respectively. These values are based on historical norms for similar elastomers as determined by conventional methods known to those skilled in the art (density gradient columns or application of Archimedes principle) and believed to be accurate to within 5% for the samples described in this application.

Engineering Strain (e) is defined as $$e = (L-L0)/L0 = z/L0$$

where:
L0 is the gauge length (i.e., the distance between lines of grip contact when the undeformed sample is mounted in the grips. The L0 in the present example is 10 mm.
Grip position, L, is the distance between lines of grip contact during the tensile test.
Displacement, z, is defined as z=L−L0.

Engineering Strain Rate is the first time derivative of the Engineering Strain, expressed in units of s⁻¹. A convenient form for calculating Engineering Strain Rate is $$\frac{d\varepsilon}{dt} = \frac{v}{Lo}$$

where:
v and L0 are the speed at which one grip moves relative to the other, and the sample's gauge length respectively.

High-Speed Tensile Strength is the maximum Engineering Stress borne by the sample reported to 3 significant digits.

Notched High-Speed Tensile Test

This method is used to measure the Tensile Strength of a notched sample at a relatively high strain rate, and is performed the same way as the High Speed Tensile Test described above, except that a 1 mm edge notch is cut into the sample before running. The notch is cut in the same manner as described above in the Slow Tear Test (i.e., perpendicular to the side edge of the sample). The sample is mounted with minimal slack & the notch centered between the grips.

Notched High-Speed Tensile Strength is the maximum Engineering Stress borne by the sample, reported to 3 significant digits.

Slow Peel and Peel Force

Materials Needed

Model Adherend: McMaster-Carr 8567K32 or similar, McMaster-Carr, Elmhurst, Ill. Polyethylene Terephthalate film 70-80 micrometers in thickness. Must meet the criterion for wettability described in the specimen preparation section, below.

Adhesive: Bostik NoCreep (H20043F), Bostik, Inc., Wauwatosa, Wis.

Cutting Pad: McMaster-Carr 70875A65 or similar.

Release Paper Single-side-coated, FRA-202 from Fox River Associates or similar, Fox River Associates, LLC, Geneva, Ill.

Printer Paper: Hammermill Copy Plus or similar (for photocopying and laser printing), International Paper, Memphis, Tenn.

Surface Tension Reagents and Swabs: Diversified Enterprises, Claremont, N.H.

Double-Sided Tape for the Slow Peel Resistance test: 3M type "9589". For example McMaster-Carr 77185A25. Any similar tape is suitable provided it holds the model adherend securely to the metal backing plate for the slow peel resistance measurement.

Metal Plate for the Slow Peel Resistance test: Stainless steel plate approximately 1.5 mm in thickness. McMaster-Carr 1421T13 or similar, cut to suitable size.

Tools

Hydraulic Press with temperature-controlled heated platens: Carver model 3853-0 or similar. Carver, Inc., Wabash, Ind.

Hand Roller: HR-100 4.5 lb. (2040 g) or similar. ICHEMCO s.r.l., via 11 Settembre, 5 20012 Cuggiono (MI), Italy. This roller has a steel core with a Shore scale A 80 durometer Silicone rubber cover. Two legs extend beyond the circumference of the roller to prevent flat spots in the rubber when the roller is stored for extend periods of time. These rollers meet the requirements of PSTC Appendage B, PSTC/AFERA/ISO/JATMA Harmonized Test Methods.

Grips for the Slow Peel Resistance test: Binder clips 1.25" in width. McMaster-Carr 12755T73 or similar.

Weight Actuated Timer for the Slow Peel Resistance test: ChemInstruments "Shear Tester" model 001816 or similar. (Timer stops when weight falls onto it.) ChemInstruments, Inc., Fairfield, Ohio.

Specimen Preparation

Figure 11:
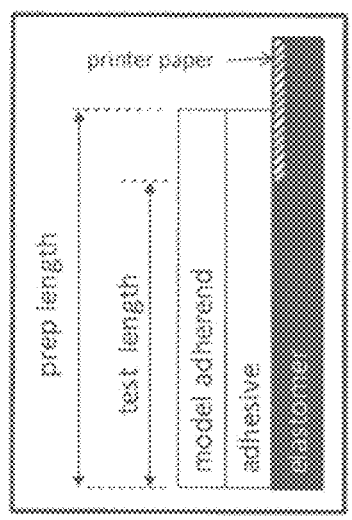
FIG. 11 is a schematic illustration of a specimen to be used in the Slow Peel and Peel Force tests described here.

1. Heat the press platens to 193° C. and hold them at this temperature for the entire specimen prep procedure.
2. All other specimen prep is carried out in a lab with an ambient temperature of 22 C+/−2 C.
3. The side of the model adherend to which the adhesive is applied should have a wetting tension of 42 dyn/cm or greater as described in ASTM D2578-09. Reagents and swabs were sourced as indicated in the materials section.
4. Determine the model adherend's basis weight by weighing appropriately representative specimens with dimensions that have been measured with the appropriate precision and accuracy.
5. Refer to the Table 6 and FIG. 11 for the following steps. During the test the adhesive joints are loaded along the "length" direction as indicated in Table 6.
6. Cut 2 sheets of release paper sized to fit in the press and cover the platens-during the molding process. Place approximately 0.1 grams of the adhesive (this amount might need to be adjusted as described in step 8 below) near the center of one sheet (release-side up) and cover with a 65 mm×120 mm sheet of model adherend, measured along the model adherend's TD and MD, respectively. Cover with a top layer of release paper (release-side down). Place entire stack into the press. Actuate the press, bringing the heated platens into contact with the stack, then gradually (over about 10 seconds) apply just enough pressure to cause the adhesive to spread uniformly over the desired prep length and width (see FIG. 11 and Table 6 specifying specimen dimensions.)
7. Remove the stack from the press. Rapidly place between flat metal plates 7 mm thick with lateral dimensions adequate to press the portion of the specimen with adhesive and hold until adhesive cools to 20-35° C.
8. Remove top layer of release paper. Use an exacto-knife, steel straight-edge and cutting pad to cut the specimen to the appropriate "prep dimensions" as indicated in the table. Use the portion of the model adherend covered most uniformly by the adhesive, determined visually through the model adherend, for the test piece. Remove release paper. Weigh the adhesive/model adherend composite. Calculate the basis weight of the adhesive/model adherend composite using the prep dimensions indicated in Table 6. Subtract the model adherend's basis weight from the adhesive/model adherend composite's basis weight to determine the adhesive's basis weight.
9. Repeat steps 3-8, adjusting press pressure, adhesive amount, and the initial arrangement of adhesive under the adherend until the adhesive is uniformly coated on the adherend and its basis weight is 22.5 gsm+/−2.5 gsm, as indicated in Table 6.
10. Use a sheet of printer paper to block the portion of the adhesive at one end of the specimen between the "prep length" and the "test length" as indicated in Table 6. This creates a break in the adhesive joint to help initiate peeling for testing. Leave the paper on the adhesive during subsequent testing.
11. Use procedures consistent with the contamination avoidance criteria given in ASTM D1876-08.
12. Cut a piece of the desired elastomer film with length and width 25 mm larger than the prep length and width respectively. Lay it on the cutting pad. Carefully lay the model adherend, adhesive side down, onto the elastomer film. Start at one end to minimize entrained air between film and adhesive. Ensure the elastomer film is placed to cover all areas of the adhesive and extends far enough beyond the paper end of the prep length to allow gripping during subsequent testing. Cover with a sheet of release paper. Use the roller to press elastomer and adhesive together, completing 10 back-and-forth cycles along the specimen's prep length. Use a rolling speed that takes about 1 second for each traverse of the prep length. No additional pressure is applied to the specimen other than exerted by the weight of the roller.

13. Use an exacto-knife, steel straight-edge and cutting pad to trim the specimen to the appropriate test width as indicated in Table 6.
14. Age the specimen at a temperature of 60° C. for 17 hours+/−1 hour.
15. Cool specimens to a temperature of 23 C+/−2 C and commence testing within 30 minutes.
16. For the slow peel test, multiple layers of office grade tape can be used to "build up" the elastomer film's thickness near its free end to give the grip a "wedge-shaped" portion to decrease the likelihood of it slipping off during the test.
17. Apply the appropriate peel test steps (see "Peel Force" and "Slow Peel," below).

like McMaster-Carr 12755T74) may be used. Report the Slow Peel Resistance as the average of three specimens.

1. This test is run at a temperature of 37.8° C. Use a suitable enclosure or room to house the apparatus, maintaining a temperature of 37.8° C. (100 F)+/−1 degree Celsius during thermal equilibration and testing.
2. Prepare and age specimen (model adherend, adhesive and elastomer film) as described in Specimen Prep section.
3. Use double-sided tape to mount specimen on rigid metal backing
4. Mount the specimen assembly (metal plate, double sided tape and specimen) in the apparatus.
5. Apply powder (corn starch or talc) to the elastomer's free surface to prevent the elastomer sticking to itself during the test.
6. Allow the specimen assembly to equilibrate thermally for 10 minutes.
7. Apply the grip and weight to the unbonded end of the elastomer film and start the timer.
8. Situate a force-actuated timer under the weight to record the time at which the peel distance traverses the specimen's test length and the elastomer film and weight fall.

TABLE 6

| Test | Prep Length (mm) | Test Length (mm) | prep width (mm) | Test width (mm) | prep area (m2) | adhesive basis wt (g/m2) | adhesive mass on prep area (grams) |
|---|---|---|---|---|---|---|---|
| Conventional Peel | 60 | 45 | 35 | 29 | 2.10E−03 | 22.5 | 0.0473 |
| Slow Peel | 60 | 50 | 54 | 48 | 3.24E−03 | 22.5 | 0.0729 |
| Corresponding Direction on Model Adherend and Elastomer Film | MD | MD | TD | TD | — | — | — |

Peel Force

This test measures the amount of force required to peel the elastomer film from the model adherend. Use ASTM D1876-08, using the following parameters. Three or more specimens shall be run. The Peel Force is the average of three specimens.

Section 4.1.3: in addition to the other criteria, the grips can accommodate specimens with unbonded ends 15 mm in length.

Section 5.2: Specimen dimensions are 60 mm×29 mm wide, with a bonded length of 45 mm, giving bonded ends 15 mm in length.

Section 6.1: Specimens are prepped and conditioned as described in the specimen prep section.

Section 7.1: Use a head speed of 0.1 mm/s (6 mm per minute.)

Section 7.3: Determine the peel resistance over at least a 25 mm length of the bond line after the initial peak.

Section 9.1.4: Average coat weight of adhesive layer as given in specimen prep section.

Slow Peel

Figures 12A, 12B:
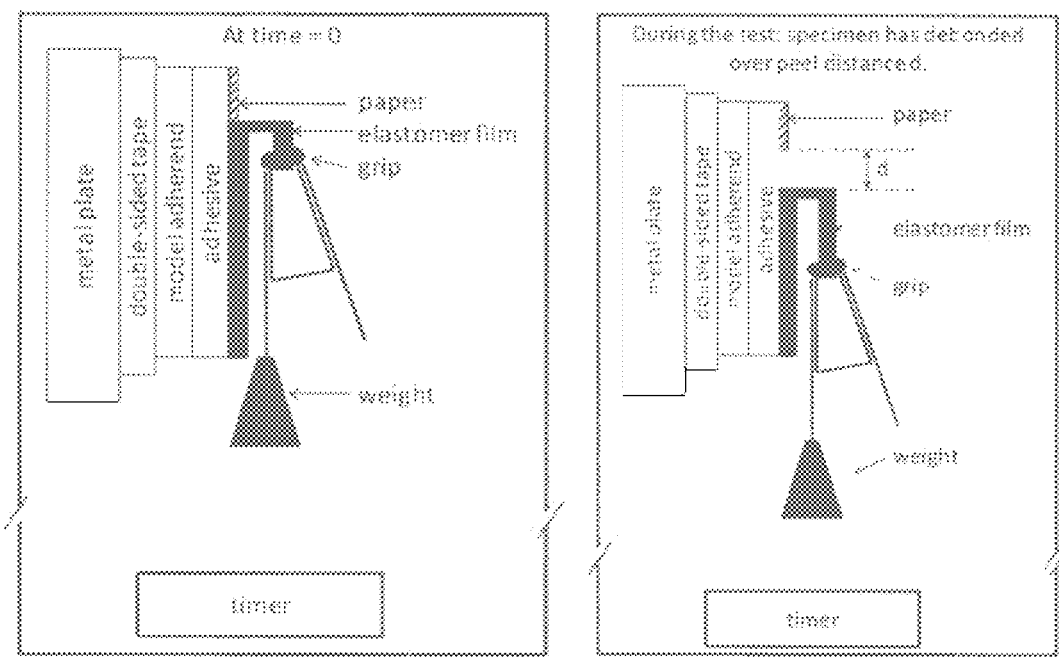
FIGS. 12A and 12B are schematic illustrations of the configuration of a specimen and weight in a Slow Peel test as described herein.

This test determines the slow peel resistance by measuring the amount of time for the peel distance to traverse the specimen's test length (see specimen prep section) when loaded with a 300 gram weight in a 180 degree peel test. Care must be taken that the grip and weight don't rub on specimen during the test. See FIGS. 12A and 12B. If a grip with a longer handle is needed, a larger binder clip (for example a 2" clip 9. The specimen's "slow peel resistance" is given as the peel time divided by the test length, expressed as seconds per micrometer. For example, a specimen that takes 4 hours (14,400 s.) to peel a distance of 50 mm (50,000 μm) would have a peel resistance of 0.288 seconds per micrometer. Inversely, it may be expressed that the specimen exhibits peel separation in the Slow Peel test at the rate of 3.47 μm/sec (the units used to report results for particular samples in Table 6).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Additionally, properties described herein may include one or more ranges of values. It is to be understood that these ranges include every value within the range, even though the individual values in the range may not be expressly disclosed.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A structure including an elastomeric film layer and an adhesive in contact therewith, wherein the elastomeric film layer comprises:
   from 53 to 65 percent by weight of a stvrene-ethylene-ethyene-propylene-styrene elastomeric block copolymer having a rubbery midblock of a hydrogenated copolymer of isoprene and butadiene;
   from 8 to 15 percent by weight of a thermoplastic polymer additive;
   from 10 to 20 percent by weight of a tackifier; and
   from 10 to 20 percent by weight of a plasticizer;
   and wherein the adhesive comprises:
   at least one homogeneous polyolefin copolymer of ethylene with propylene or alpha olefins;
   up to 60 percent by weight of a tackifier; and
   up to 15 percent by weight of a plasticizer.

2. The structure of claim 1 wherein the adhesive comprises a Hot Melt Adhesive.

3. The structure of claim 1 wherein the tackifier has a molecular weight Mn from 500 g/mol to 2000 g/mol.

4. The structure of claim 1 wherein the plasticizer is selected from the group consisting of mineral oil; naphthenic oils; paraffinic oils; olefin oligomers and low molecular weight polymers; vegetable oils; animal oils; petroleum derived waxes; and mixtures thereof.

5. The structure of claim 1 wherein the thermoplastic polymer additive comprises a composition selected front the group consisting of polyphenylene oxide and vinylarene polymers derived from monomers including styrene, alpha-methyl styrene, para-methyl styrene, other alkyl styrene derivatives, vinyl toluene, and mixtures thereof.

6. A structure including an elastomeric film layer and an adhesive in contact therewith, wherein the elastomeric film layer comprises:
   a styrene-ethylene-ethylene-propylene-styrene elastomeric block copolymer having a rubbery midblock of a hydrogenated copolymer of isoprene and butadiene;
   a thermoplastic polymer additive;
   a tackifier in an amount greater than 7 percent by weight of the elastomeric film layer; and
   a plasticizer;
   and wherein the adhesive comprises:
   from 10 to 45 percent by weight of a block copolymer;
   from 40 to 80 percent by weight of a tackifier: and
   up to 15 percent by weight of a plasticizer.

7. The structure of claim 6 wherein the adhesive comprises a Hot Melt Adhesive.

8. The structure of claim 6 wherein the tackifier molecular weight Mn from 500 g/mol to 2000 g/mol.

9. The structure of claim 6 wherein the plasticizer is selected from the group consisting of mineral oil; naphthenic oils; paraffinic oils; olefin oligomers and low molecular weight polymers; vegetable oils; animal oils; petroleum derived waxes; and mixtures thereof.

10. The structure of claim 6 exhibiting a Slow Peel Resistance no greater than 2.0 μm/s.

11. The structure of claim 6 exhibiting a Peel Force greater than 5.0 N/mm.

12. A structure including an elastomeric film layer and an adhesive in contact therewith, wherein the elastomeric film layer comprises:
   a styrene-ethylene-ethylene-propylene-styrene elastomeric block copolymer having a rubbery midblock of a hydrogenated copolymer of isoprene and butadiene;
   a thermoplastic polymer additive;
   a tackifier in an amount greater than 7 percent by weight of the elastomeric film layer; and
   a plasticizer;
   and wherein the adhesive comprises:
   at least one homogeneous polyolefin copolymer of ethylene with propylene or alpha olefins;
   up to 60 percent by weight of a tackifier; and
   up to 15 percent by weight of a plasticizer.

* * * * *